US008119854B2

(12) United States Patent
Sanna

(10) Patent No.: US 8,119,854 B2
(45) Date of Patent: Feb. 21, 2012

(54) ROLE OF PROTEOGLYCANS IN DRUG DEPENDENCE

(75) Inventor: Pietro Paolo Sanna, San Diego, CA (US)

(73) Assignee: Pietro P. Sanna, San Diego, CA (US)

( * ) Notice: Subject to any disclaimer, the term of this patent is extended or adjusted under 35 U.S.C. 154(b) by 541 days.

(21) Appl. No.: 12/085,381

(22) PCT Filed: Nov. 21, 2006

(86) PCT No.: PCT/US2006/045078

§ 371 (c)(1),
(2), (4) Date: Mar. 2, 2009

(87) PCT Pub. No.: WO2007/062048

PCT Pub. Date: May 31, 2007

(65) Prior Publication Data

US 2010/0199361 A1 Aug. 5, 2010

Related U.S. Application Data

(63) Continuation-in-part of application No. 11/149,937, filed as application No. PCT/US03/39499 on Dec. 10, 2003.

(60) Provisional application No. 60/738,913, filed on Nov. 21, 2005, provisional application No. 60/739,793, filed on Nov. 23, 2005, provisional application No. 60/783,492, filed on Mar. 17, 2006, provisional application No. 60/432,496, filed on Dec. 10, 2002.

(51) Int. Cl.
*A01K 67/00* (2006.01)

(52) U.S. Cl. .......................................................... 800/9

(58) Field of Classification Search ........................ None
See application file for complete search history.

(56) References Cited

U.S. PATENT DOCUMENTS

| | | | |
|---|---|---|---|
| 4,938,949 | A | 7/1990 | Borch et al. |
| 5,053,133 | A | 10/1991 | Klein et al. |
| 5,116,750 | A | 5/1992 | Gelfand et al. |
| 5,168,049 | A | 12/1992 | Meade et al. |
| 5,595,887 | A | 1/1997 | Coolidge et al. |

FOREIGN PATENT DOCUMENTS

WO WO2004/053099 * 6/2004

OTHER PUBLICATIONS

Strader et al (Journal of Clinical Investigation. Nov. 1, 2004; 114(9): 1354-1360).*

Ahmed et al., Persistent Increase in the Motivation to Take Heroin in Rats with a History of Drug Escalation, Neuropsychopharmacology, 2000, 413-421, 22(4).

Ahmed et al., Neurobiological evidence for hedonic allostasis associated with escalating cocaine use, Nat. Neurosci., 2002, 625-626, 5(7).

Alvaro et al., Melanocortins and opiate addiction, Life Sci., 1997, 1-9, 61(1).

Alvaro et al., Molecular and behavioral interactions between central melanocorins and cocaine, J. Pharmacol. Exp. Ther., 2003, 391-399, 304(1).

Asundi et al., Matrix metalloproteinase-dependent shedding of syndecan-3, a transmembrane heparan sulfate proteoglycan, in Schwann cells, J. Neurosci. Res., 2003, 593-602, 73(5).

Bandtlow et al., Proteoglycans in the developing brain: new conceptual insights for old proteins, Physiol. Rev., 2000, 1267-1290, 80(4).

Bhargava, Opioid peptides, receptors, and immune function, NIDA Res. Monogr., 1990, 220-233, 96.

Cantallops et al., Synapse formation: if it looks like a duck and quacks like a duck, Curr. Biol., 2000, R620-623, 10 (17).

Carlezon Jr. et al., Sensitization to morphine induced by viral-mediated gene transfer, Science, 1997, 812-814, 277(5327).

Carlezon Jr. et al., Repeated exposure to rewarding brain stimulation downregulates GluR1 expression in the ventral tegmental area, Neuropsychopharmacology, 2001, 234-241, 25(2).

Chapman et al., Fractalkine cleavage from neuronal membranes represents an acute event in the inflammatory response to excitotoxic brain damage, J. Neurosci., 2000, RC87 pp. 1-5, 20(15).

Chen et al., Anthranilate sulfonamide hydroxamate TACE inhibitors. Part 1: Structure-based design of novel acetylenic P1' groups, Bioorg. Med. Chem. Lett., 2002, 1195-1198, 12(8).

Conway et al., Inhibition of Tumor Necrosis Factor-α (TNF-α) Production and Arthritis in the Rat by GW3333, a Dual Inhibitor of TNF-α-Converting Enzyme and Matrix Metalloproteinases, J. Pharmacol. Exp. Ther., 2001, 900-908, 298(3).

Cull-Candy et al., NMDA receptor subunits: diversity, development and disease, Curr. Opin. Neurobiol., 2001, 327-335, 11(3).

De La Garza et al., The discriminative stimulus properties of cocaine in the rhesus monkeys, Pharmacol. Biochem. Behav., 1983, 145-148, 19(1).

De La Garza et al., Discriminative stimulus properties of cocaine in pigeons, Psychopharmacy (Berl)., 1985, 23-30, 85(1).

De Vries et al., Neural systems underlying opiate addiction, J. Neurosci., 2002, 3321-3325, 22(9). Duan et al., Discovery of gamma-lactam hydroxamic acids as selective inhibitors of tumor necrosis factor alpha converting enzyme: design, synthesis, and structure-activity relationships, J. Med. Chem., 2002, 4954-4957, 45(23).

Fitzgerald et al., Shedding of Syndecan-1 and -4 Ectodomains Is Regulated by Multiple Signaling Pathways and Mediated by a Timp-3—Sensitive Metalloproteinase, J. Cell Biol., 2000, 811-824, 148(4).

Forquer et al., Inhibition of matrix metalloproteinase activity attenuates acquisition and exteinction of cocaine-induced conditioned place preference in rats, Program No. 581.7; 2004 Abstract Viewer/Itinerary Planner Society for Neuroscience, Washington, D.C., 2004, 1 page.

Hawley's Condensed Chemical Dictionary, 2001, p. 283, John Wiley & Sons, Inc.

Huang et al., Constitutive activation of stat 3 oncogene product in human ovarian carcinoma cells, Gynecol. Oncol, 2000, 67-73, 79(1).

Johanson et al., The Discriminative Effects of Cocaine in Pidgeons, J. Pharm. Exp. Ther., 1993, 1-8, 267(1).

(Continued)

*Primary Examiner* — Scott Long

(74) *Attorney, Agent, or Firm* — Acuity Law Group; Douglas C. Murdock

(57) ABSTRACT

The invention provides methods of preventing or treating drug addiction, or ameliorating the craving for an addictive drug, as well as compounds, peptides, and pharmaceutical compositions that may be used to prevent or treat drug addiction or ameliorate the craving for an addictive drug. The invention also provides methods for identifying agents that may be used to prevent or treat drug addiction, or ameliorate the craving for an addictive drug.

7 Claims, 7 Drawing Sheets

OTHER PUBLICATIONS

Kawai et al., Axonal contact regulates expression of alpha2 and beta2 isoforms of Na+, K+-ATPase in Schwann cells: adhesion molecules and nerve regeneration, J. Neurochem., 1997, 330-339, 69(1).

Koob et al., Neuroscience of Addiction, Neuron, 1998, 467-476, 21(3).

Koob et al., Neurobiology of Addiction: Chapter 3: Psychostimulants, 2006, Elsevier, Inc., London, UK, ISBN-13:978-0-12-419239-3/ISBN-10:0-12-419239-4, 5 pgs.

Kreek et al., Pharmacotherapy of addictions, Nat. Rev. Drug Disc., 2002, 710-726, 1(11).

Lee et al., Opioid receptor polymorphisms and opioid abuse, Pharmacogenomics, 2002, 219-227, 3(2).

Letavic et al., Synthesis and biological activity of piperazine-Based dual MMP-13 and TNF-α converting enzyme inhibitors, Bioorg. Med. Chem. Lett., 2003, 3243-3246, 13(19).

Levitzki, Protein tyrosine kinase inhibitors as novel therapeutic agent, Pharmacol. Ther., 1999, 231-239, 82(2-3).

Lindblom et al., Alcohol-preferring AA rats show a derangement in their central melanocortin signalling system, Pharmacol. Biochem. Behav., 2002, 491-496, 72(1-2).

Nestler et al., Molecular and cellular basis of addiction, Science, 1997, 58-63, 278(5335).

Ploj et al., Effects of melanocortin receptor ligands on ethanol intake and opioid peptide levels in alcohol-preferring AA rats, Brain Res. Bull., 2002, 97-104, 59(2).

Reizes et al., Syndecan-3 modulates food intake by interacting with the melanocortin/AgRP pathway, Ann. N.Y. Acad. Sci., 2003, 66-73, 994.

Sharon et al., Plasminogen mRNA induction in the mouse brain after kainate excitation: codistribution with plasminogen activator inhibitor-2 (PAI-2) mRNA, Brain Res. Mol. Brain Res., 2002, 170-175, 104(2).

Sims et al., Platelet-derived growth factor rapidly increases activity and cell surface expression of the EAAC1 subtype of glutamate transporter through activation of phosphatidylinositol 3-kinase, J. Biol. Chem., 5228-5237, 275(7).

Stamenkovic, Extracellular matrix remodelling: the role of matrix metalloproteinases, J. Pathol., 2003, 448-464, 200 (4).

Stephanou et al., Opposing actions of STAT-1 and STAT-3 on the Bcl-2 and Bcl-x promoters, Cell Death Differ., 2000, 329-330, 7(3).

Taber's Cyclopedic Medical Dictionary, 19th Ed., 2001, pp. 1356-1357 and 1448-1449, F.A. Davis Company, Philadelphia, PA.

Wang et al., rGbetal: a psychostimulant-regulated gene essential for establishing cocaine sensitization, J. Neurosci., 1997, 5993-6000, 17(15).

* cited by examiner

Syndecan-3 peptide

ROLE OF PROTEOGLYCANS IN DRUG DEPENDENCE

REFERENCE TO EARLIER PATENT APPLICATIONS

This application is a U.S. National Stage filing under 35 U.S.C. 371 from International Application No. PCT/US2006/045078 filed Nov. 21, 2006 and published in English as WO 2007/062048 on May 31, 2007, which claims the benefit of U.S. Provisional Patent Application Ser. No. 60/738,913 filed Nov. 21, 2005; U.S. Provisional Patent Application Ser. No. 60/739,793 filed Nov. 23, 2005; and U.S. Provisional Patent Application Ser. No. 60/783,492 filed Mar. 17, 2006; which applications and publication are incorporated herein by reference in their entirety.

This application is also a continuation-in-part of U.S. patent application Ser. No. 11/149,937 filed Jun. 10, 2005, which is a U.S. National Stage filing from International Application No. PCT/US03/39499 filed Dec. 10, 2003 and published in English as WO 2004/053099 on Jun. 24, 2004, which claims the benefit of U.S. Provisional Application Ser. No. 60/432,496 filed Dec. 10, 2002, which applications and publication are incorporated herein by reference in their entirety.

STATEMENT REGARDNG FEDERALLY SPONSORED RESEARCH

Work relating to this application was supported by a grant from the U.S. Government (5R21NS047753-02). The government may have certain rights in the invention.

TECHNICAL FIELD

The invention relates to treatments for drug addiction.

BACKGROUND

Society has devoted significant efforts toward ameliorating the deleterious effects of compulsive drug use such as antisocial behavior, physiological addiction, physical debilitation, contraction of diseases and ultimately death. Use of hospitalization, counseling, treatment programs and withdrawal management have been part of continuing attempts to minimize the impact of addiction. Yet drug addiction continues to be an ongoing problem among adolescents and adults alike.

Researchers who have studied the biological basis of drug addiction have found that the painful withdrawal and frequent relapse could be attributed to significant physiopathological alterations that take place as a result of drug use. Therefore, methods of managing or treating drug addiction that are directed to the molecular mechanisms responsible for the development of compulsive drug use, craving and relapse after abstinence, as well as screening methods which take into account such mechanisms for drug discovery, would be useful for effective management and treatment of addiction, withdrawal and relapse to drug taking.

SUMMARY OF THE INVENTION

The invention provides methods for preventing or treating drug addiction, or ameliorating the craving for an addictive drug in a mammal. The invention also provides purified oligopeptides, other small molecules, and pharmaceutical compositions and articles of manufacture thereof that could be used to prevent or treat drug addiction, or ameliorate the craving for an addictive drug. The invention also provides methods for identifying an agent effective for preventing or treating drug addiction.

Methods and compositions of the invention can be used to prevent or treat drug addiction, as well as ameliorate the craving for an addictive drug during abstinence so as to prevent or reduce the likelihood of relapse or re-addiction. An addictive drug includes any drug of abuse. Examples include, without limitation, stimulants like cocaine, amphetamine and methamphetamine; narcotics such as opium, its derivatives and semi-synthetic substitutes; depressants such as alcohol, gamma hydroxybutyric acid, barbiturates and benzodiazepines; nicotine; hallucinogens such as Lysergic acid diethylamide (LSD) and 3-4 Methylenedioxymethamphetamine (MDMA, commonly known as ecstasy); cannabinoid drugs such as marijuana, hashish and hashish oil, and other synthetic and designer drugs. See web site www.usdoj.gov/dea/concern/concern.htm for more information on, other drugs of abuse.

Without intending to limit the scope of the invention, we have discovered that when cocaine is made available for a short period of time, syndecan-3 knockout mice self-administer significantly more cocaine than mice transgenically expressing the ectodomain (cleavage product) of syndecan-1 and mice expressing the whole (full-length) syndecan-1 transgene. When cocaine is made available for a longer period of time, the amount of cocaine intake by syndecan-3 knockout mice and mice expressing the ectodomain (cleavage product) of syndecan-1 escalate significantly early on. In contrast, cocaine intake by mice expressing the whole (full-length) syndecan-1 transgene do not escalate under extended access conditions. The resistance to escalating cocaine intake demonstrated by whole (full-length) syndecan-1 transgenic mice may be attributed to the absence of protease cleavage of syndecan-1 by a protease such as, for example, a sheddase, matrix metalloproteases (MMP), ADAM (e.g. a disintegrin and metalloproteinase and adamlysins). Consistent with this hypothesis is the finding that mice transgenic for the ectodomain of syndecan-1 were not resistant to escalating cocaine intake, while mice transgenic for the full length syndecan-1, which is resistant to cleavage when expressed in the brain, were resistant to escalating cocaine intake under extended access conditions.

Syndecan-3 knockout mice and mice expressing the ectodomain of syndecan-1 respond significantly more to cue-induced reinstatement of cocaine-seeking behavior than whole (full-length) syndecan-1 transgenic mice. These findings indicate that syndecan processing is involved in both initial susceptibility to drug addiction as well as addiction and craving during withdrawal and relapse. These findings suggest that inhibitors of syndecan-3 processing, such as tissue inhibitors of metalloproteases, oligopeptides and other small molecules can be useful for the prevention and treatment of drug addiction, as well as the amelioration of craving for an addictive drug. In addition, syndecan-1 or non-cleavable variants of syndecan-3, as well as functional fragments of these polypeptides, would be useful for the prevention and treatment of drug addiction, as well as the amelioration of craving for an addictive drug.

Therefore, in one embodiment, the invention provides a method for preventing or treating drug addiction, or ameliorating the craving for an addictive drug, in a mammal that involves administering an agent that inhibits proteolytic cleavage of syndecan-3 in the mammal. The agent may be a sheddase inhibitor, more specifically, a matrix metalloprotease inhibitor (MMP) or an inhibitor of disintegrin and metalloprotease (ADAM) or other protease involved in the cleavage of syndecan-3 ectodomain or a protease required for the activation of a protease involved in the cleavage of syndecan-3 ectodomain. A MMP inhibitor may be a peptidic succinyl inhibitor, a N-carboxyalkyl peptidic inhibitor, and a malonic acid-based hydroxamic acid inhibitor. MMP inhibitor may also be a small molecule such as, for example, a succinate peptidemimetic compound, a succinate macrocyclic compound, a non-peptidic sulfonamide, a sulfone hydroxamate, a thiol, a reverse hydroxamic acid, a ketone and a phosphorous-based compound. Other examples of inhibitors include, without limitation, iliomastat, marimastat, prinomastat, trocade, PKF24-484, and INCB7839. Other inhibitors may be a polypeptide such as, for example, a tissue inhibitor metalloprotease (TIMP) e.g., TIMP-1, TIMP-2, TIMP-3, or a biologically active fragment of these such as an oligopeptide of 4 to about 10 amino acid units in length or its derivatives, which has a sequence mimicking that of the epitopal region of these polypeptides. Other inhibitors may also be a substrate of a proteinase in order to block the active site of a proteinase, and/or chelate $Zn^{2+}$ or other metal essential for proteinase activity.

In another embodiment, the invention provides a method for preventing or treating drug addiction, or ameliorating the craving for an addictive drug, in a mammal involving increasing the level of one or more of the following polypeptide(s): tissue inhibitor metalloprotease-1 (TIMP-1), tissue inhibitor metalloprotease-2 (TIMP-2), tissue inhibitor metalloprotease-3 (TIMP-3), syndecan-1 and a biologically-active fragment of these, e.g. a pentapeptide.

In another embodiment, the in vivo level of one or more of the above polypeptide(s) may be increased by contacting the mammal with a vector encoding the one or more polypeptide(s), or a biologically active fragment thereof, operably linked to transcriptional regulatory control sequence such as a promoter, e.g. a viral promoter. The vector may be a viral vector such as, for example, a retroviral vector, a lentiviral vector, a herpes virus vector an adenoviral vector, an adeno-associated viral vector or other viral or non-viral gene-delivery system.

In another embodiment, the invention provides a method for preventing or treating drug addiction, or ameliorating the craving for an addictive drug, in a mammal that involves administering an agent that inhibits syndecan-3 glycosylation. An agent that inhibits syndecan-3 glycosylation may be an agent that inhibits N-acetylgalactosaminyltransferase such as a nucleosidyl shift base.

In another embodiment, the invention provides an article of manufacture that includes packaging material and, contained within the packaging material, a sheddase inhibitor. A sheddase inhibitor may be a MMP inhibitor, an ADAMs inhibitor or an inhibitor of other protease involved in the cleavage of syndecan-3 ectodomain. In a further embodiment, the packaging material can have a label indicating that the sheddase inhibitor is usable for preventing or treating drug addiction, or ameliorating the craving for an addictive drug.

In another embodiment, the invention provides an oligopeptide having from four to ten amino acid units in its sequence or a derivative of such a peptide, as well as a pharmaceutical composition having a pharmaceutically acceptable carrier and an oligopeptide of four to ten amino acid units in its sequence. The sequence of the oligopeptide may mimic the active site region of TIMP-2 or TIMP-3 or the sequence of proteinase substrate or a sequence otherwise capable of blocking the activity of said proteinase.

In another embodiment, the invention provides a method for screening and identifying an agent effective for preventing or treating drug addiction or ameliorating the craving for an addictive drug that involves (a) administering a test compound to a test animal and (b) determining the level of syndecan-3 cleavage in the animal such that if the level of syndecan-3 cleavage is lowered relative to a control, then the test compound is an agent effective for preventing drug addiction, treating drug addiction or ameliorating the craving for an addictive drug. The level of syndecan-3 cleavage in the animal may be determined from the level of full-length syndecan-3 or the level of the ectodomain of syndecan-3 in the brain of the animal, e.g. in the hypothalamus. A control for comparison can be another animal of the same species.

In another embodiment, the invention provides a method for screening for an agent effective for preventing or treating drug addiction or ameliorating the craving for an addictive drug that involves (a) administering a test compound to a syndecan-3 knockout mouse; and (b) determining whether the test compound reduces self-administration of the addictive drug in the mouse or ameliorates one or more indices of motivation for the drug. Indices of motivation for the drug include one or more of the following: drug reward, anxiety and stress associated with withdrawal and abstinence, craving for the drug, reinstatement of drug taking after a period of abstinence induced by to presentation of a drug associated cue, stress, priming by non-contingent administration of the drug, conditioned place preference, escalation of drug intake, and a shift in the cocaine dose-response curve as described herein.

In another embodiment, the invention provides an animal model for screening for compounds that will decrease the craving for an addictive drug in a human. The animal model is a syndecan-3 knockout mouse that exhibits (a) an increase frequency of self-administration of the addictive drug, or (b) an increase in one or more of the indices of motivation for the drug relative to a mouse of the same species that is transgenic for the whole (full-length) syndecan-1 or the syndecan-1 ectodomain.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. The present specification provides selected definitions of certain terms, and these definitions are preferred relative to other definition in the event that there are discrepancies. In addition, the materials, methods, and examples are illustrative only and not intended to be limiting.

Other features and advantages of the invention will be apparent from the following description and from the claims. The invention will be further described in the following examples, which do not limit the scope of the invention described in the claims.

BRIEF DESCRIPTION OF DRAWINGS

In FIG. 1A gene expression levels in various regions of the brain are graphed illustrating the escalation of intravenous cocaine consumption in rats given short access (ShA) to cocaine self-administration.

FIG. 3B is a graph comparing total cocaine intake over six hours by syndecan-3 knockout mice, whole (full-length) syndecan-1 transgenic mice and mice expressing synecan-1 ectodomain over eight days. FIG. 3C illustrates the more pronounced shift towards earlier loading seen in syndecan-3 knockout mice compared to wild-type mice when the first and eighth day of long access to cocaine were compared. FIG. 3D is a bar graph illustrating selectiveness for the active lever demonstrated by responses of syndecan-3 knockout mice, whole (full-length) syndecan-1 transgenic mice and mice expressing synecan-1 ectodomain. FIG. 3E is a bar graph comparing the effort with which syndecan-3 knockout mice, whole (full-length) syndecan-1 transgenic mice and mice expressing syndecan-1 ectodomain were willing to expend to obtain cocaine.

FIG. 4A is a graphical comparison of the reinstatement responses of syndecan-3 knockout mice, whole (full-length) syndecan-1 transgenic mice and mice expressing syndecan-1 ectodomain on the active lever as a result of presentation of a cue light that was previously associated cocaine infusion. FIG. 4B is a graphical comparison of the reinstatement responses of syndecan-3 knockout mice, whole (full-length) syndecan-1 transgenic mice and mice expressing synecan-1 ectodomain on the inactive lever as a result of presentation of a cue light that was previously associated cocaine infusion. FIG. 4C is a graphical comparison of the % responses at the active lever by syndecan-3 knockout mice, whole (full-length) syndecan-1 transgenic mice and mice expressing syndecan-1 ectodomain as a result of presentation of a cue light that was previously associated cocaine infusion showing a greater persistence of responding on the active lever by syndecan-3 knockout mice.

FIG. 5A is a western blot that shows that administration of GM6001 to mice reduces shedding of syndecan-3 using a syndecan-3 C-terminal domain-specific antibody.

FIG. 6A is a graph that shows inhibition of cocaine-seeking behavior by GM6001.

FIG. 7A shows overlapping fluoregenic peptides spanning the juxta-membrane region of the mouse syndecan-3 (Amino Acid residues 355-388; Seq. Id. No 1) and labeled with Abz and EDDnp.

DETAILED DESCRIPTION OF THE INVENTION

Figure 1:
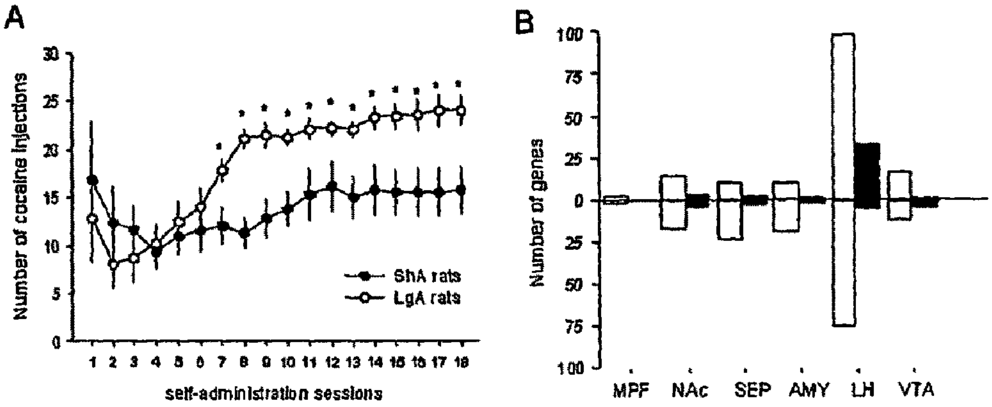
FIGS. 1A and B disclose effects of access to cocaine self-administration on drug intake (short access (ShA), and long access (LgA), respectively.
FIG. 1B is a bar graph illustrating the total number of genes per brain region that change significantly when LgA rat brains were compared to that of drug-naive control rats (white bars) and to that of ShA and drug-naive rats (black bars).

Without intending to limit the scope of the invention, in one embodiment the invention provides a method of treating drug addiction and preventing addictive drug behavior that involves administering to a patient in need thereof an effective amount of a molecule or group of molecules that is/are involved in the inhibition of cleavage of syndecan-3 and/or an increase or production of syndecan-1 levels. In a related embodiment, the invention is derived from the observation that when cocaine is made available for a short period of time, syndecan-3 knockout mice self-administer significantly more cocaine than wild-type mice transgenically expressing the ectodomain (cleavage product) of syndecan-1 and mice expressing the whole (full-length) syndecan-1 transgene. When cocaine is made available for a longer period of time, the amount of cocaine intake by syndecan-3 knockout mice and wild-type mice expressing the ectodomain (cleavage product) of syndecan-1 escalated significantly early on. Also, mice transgenic for the ectodomain of syndecan-1 were not resistant to escalating cocaine intake. In contrast, cocaine intake by mice expressing the whole (full-length) syndecan-1 transgene do not escalate cocaine intake under extended access conditions. The resistance to escalating cocaine intake demonstrated by whole syndecan-1 transgenic mice can reasonably be attributed to the absence of protease cleavage of syndecan-1 by a protease such as, for example, a sheddase or matrix metalloproteases (MMP).

In a second embodiment, the invention provides a method of treating a patient for drug addiction that involves administering to the patient a composition that includes an inhibitor of syndecan-3 processing. In a related embodiment, the invention is derived from the discovery that syndecan-3 knockout mice and mice expressing the ectodomain of syndecan-1 respond significantly more to cue-induced reinstatement of cocaine-seeking behavior than whole (full-length) syndecan-1 transgenic mice. By cue-induced is meant behavior of seeking drug based on the animal subject's effort to obtain drug, such as by having to push a lever in response to a light stimulus. These findings indicate that syndecan processing is involved in both initial susceptibility to drug addiction as well as addiction and craving during withdrawal and relapse. These findings suggest that inhibitors of syndecan-3 processing, such as tissue inhibitor metalloproteases, oligopeptides and other small molecules can be useful for the prevention and treatment of drug addiction, as well as the amelioration of craving for an addictive drug. In addition, syndecan-1 or non-cleavable variants of syndecan-3, as well as functional fragments of these polypeptides, would be useful for the prevention and treatment of drug addiction, as well as the amelioration of craving for an addictive drug. Thus, in one embodiment, the invention provides inhibitor molecules of syndecan-3 processing.

The invention also provides a method for preventing or treating drug addiction, or ameliorating the craving for an addictive drug, in a mammal. In such embodiment, the method involves administering to said mammal an agent that inhibits proteolytic cleavage of syndecan-3 in the mammal.

In another embodiment, the invention provides a method for preventing or treating drug addiction, or ameliorating the craving for an addictive drug, in a mammal comprising increasing the level of one or more of the following polypeptide(s): tissue inhibitor metalloprotease-1(TIMP-1), tissue inhibitor metalloprotease-2 (TIMP-2), tissue inhibitor metalloprotease-3 (TJMP-3), syndecan-1 and a biologically-active fragment of these, e.g. an oligopeptide, including a peptide having between 4 and 30 contiguous amino acids, e.g. a pentapeptide. Increasing amounts of or effective activity of any one of the above is accomplished by administration of said compounds to said mammal at a pharmaceutically effective amount.

In another embodiment, the in vivo level of one or more of the above polypeptide(s) may be increased by contacting the mammal with a vector encoding the one or more polypeptide(s), or a biologically active fragment thereof, operably linked to transcriptional regulatory control sequence such as a promoter, e.g. a viral promoter. The vector may be a viral vector such as, for example, a retroviral vector, a lentiviral vector, a herpes virus vector an adenoviral vector, an adeno-associated viral vector or other viral or non-viral gene-delivery system.

In another embodiment, the invention provides a method for preventing or treating drug addiction, or ameliorating the craving for an addictive drug, in a mammal that involves administering an agent that inhibits syndecan and can, for example, be an agent that inhibits N-acetylgalactosaminyltransferase such as a nucleosidyl shift base.

Inhibitor of the Invention

An inhibitor of the invention includes any small molecule, peptide or oligopeptide discussed herein that may be used to practice a method of the invention. An inhibitor of the invention may be a sheddase inhibitor, more specifically, a matrix metalloprotease inhibitor (MMP) or an inhibitor of disintegrin and metalloprotease (ADAM) or other protease involved in the cleavage of syndecan-3 ectodomain. Thus, an inhibitor of the invention is an inhibitor of MMP processing including processing of syndecan-3. An inhibitor of the invention can be any small molecule inhibitor or oligopeptide described herein that can be used to practice a method of the invention.

A MMP inhibitor may be a peptidic succinyl inhibitor, a N-carboxyalkyl peptidic inhibitor, and a malonic acid-based hydroxamic acid inhibitor as disclosed in: Skiles et al. Current Medicinal Chemistry 8: 425-74 (2001) and Skiles et al. Current Medicinal chemistry Current Medicinal Chemistry 11: 2911-2977, (2004). MMP inhibitor may also be a small molecule such as, for example, a succinate peptidemimetic compound, a succinate macrocyclic compound, a non-peptidic sulfonamide, a sulfone hydroxamate, a thiol, a reverse hydroxamic acid, a ketone and a phosphorous-based compound, also disclosed in Skiles et al. Examples of inhibitors include, without limitation, ilomastat; marimastat (BB-2516); prinomastat (AG3340); trocade; batimastat; BAY 12-9566; BMS-275291 and doxycycline further disclosed in Skiles et al. Other examples include COL-3 (see Skiles et al. Current Medicinal Chemistry 8: 425-74 (2001) and 11: 2911-77 (2004) and Rao, Current Pharmaceutical Design 11: 295-322 (2005); neovastat (see Gingras et al., Anticancer Drugs 14: 91-6 (2003)); Ro-28-2653 (Pascal et al., J. Pharm Pharmaceut Sci. 8:164-75 (2005)); ABT-518 (see Rao, Current Pharmaceutical Design 11:295-322 (2005); N-acetyl-cysteine; TSR-1265 (Silletti et al., PNAS 98: 119-24 (2001)); SI 27 (Noha et al., Journal of Neuro-Oncology 48: 217-23 (2000)); MMI-166 ((2R)-3-(1H-Indol-3-yl)-2-[4-(2-phenyl)-2H-tetrazol-5-yl]benzenesulfonylamino]propionoc acid; see Tamura et al., J. Med. Chem. 41:640-49 (1998)); MMI-270 (CGS-27023A) (see MacPherson et al. in J. Med. Chem. 40:2525-32); FYK-1388 (see Shinoda et al., International Journal of Oncology 22: 281-288 (2003)); FR255031 (see Ishikawa et al., British Journal of Pharmacology 144: 133-43 (2005)); SB-3CT (see Kleifeld et al., The Journal of Biological Chemistry 276: 17125-31 (2001)); and Ro 32-3555 (see Brown & Whittaker, available at website www.biotech-medecine.com/archives/review09 (last retrieved Jan. 4, 2006).

An inhibitor of the invention can also be a polypeptide such as a tissue inhibitor metalloprotease (TIMP), e.g. TIMP-2, TIMP-3 or a biologically active fragment of these such as an oligopeptide of 4 to about 10 amino acid units in length or its derivatives, which has a sequence mimicking that of the epitopal region of these polypeptides. An inhibitor may also be a substrate of a proteinase in order to block the active site of a proteinase, and/or chelate $Zn^{2+}$ or other metal essential for proteinase activity.

Thus, methods of the invention can be practiced using a large variety known MMP inhibitors and classes of inhibitor-active compounds. These include, without limitation, (1) the first generation MMP inhibitors, which are peptidic in nature and mimic the cleavage sites of MMP substrates, and the second generation MMP inhibitors, which are nonpeptidic in nature and are designed on the basis of the conformation of the MMP active site (See Rao, Current Pharmaceutical Design 11: 295-322 (2005) and Skiles et al. in Current Medicinal Chemistry 11: 2911-77 (2004)); (2) gelatinase A inhibitors (see Auge et al. in Critical Reviews in Oncology/Hematology 49: 277-282 (2004)); and (3) succinate peptidomimetic inhibitors, succinate macrocyclic inhibitors, sulfonamide inhibitors, sulfone hydroxamate inhibitors, thiol inhibitors, reverse hydroxamic acid inhibitors, ketone inhibitors, and phosphorus-based inhibitors as well as other miscellaneous inhibitors (see Skiles et al. in Current Medicinal Chemistry 425-74 (2001). MMP inhibitors may also include chemically-modified tetracyclines (CMTs) such as CMT-300 [6-dimethyl-6-deoxy-4-de(dimethylamino)tetracycline; CMT-3, COL-3] and CMT-308 [9-amino-6-demethyl-6-deoxy-4-de(dimethylamino)tetracycline; COL-308]. See Kocer et al., Infection and Immunity 73: 7548-57 (2005). Other examples are described in U.S. Pat. Nos. 5,837,696; 5,977,091 and 5,773,430.

An inhibitor of the invention may be an MMP inhibitor such as (1) anti-matrix metalloproteinase DNAzymes as described in U.S. Pub. Application No. 2006/0019914A1; (2) substituted biaryl oxobutyric acids as described in U.S. Pub. Application No. 2005/0267102A1; (3) tetracycline derivatives as described in U.S. Pub. Application No. 2005/0256081A1; (4) aromatic sulfone hydroxamic acids as described in U.S. Pub. Application No. 2005/0101641A1; (5) hydantoins and related heterocycles as described in U.S. Pub. Application No. 2005/0171096A1; (6) N-substituted-n-sulfonylaminocyclopropane compounds as described in U.S. Pub. Application No. 2005/0222146A1; (7) pyrido[3,4-d]pyrimidine derivatives as described in U.S. Pub. Application No. 2005/0085447A1; (8) substituted 1,3-dihydro-imidazol-2-one and 1,3-dihydro-imidazol-2-thione derivatives as described in U.S. Pub. Application No. 2005/0075384A1; (9) sulfonyl aryl or heteroaryl hydroxamic acid compounds as described in U.S. Pub. Application No. 2005/0075374A1; (10) thiol sulfonamide inhibitors as described in U.S. Pub. Application No. 2005/0014840A1; (11) fluorothiophene derivatives as described in U.S. Pub. Application No. 2005/

0014817A; (12) thiophene amino acid derivatives as described in U.S. Pub. Application No. 2005/0014816A1; (13) piperidinyl-and piperazinyl-sulfonylmethyl hydroxamic acids as described in U.S. Pub. Application No. 2005/0009838A1; (14) pyrimidine-4,6-dicarboxylic acid diamide as described in U.S. Pub. Application No. 2005/0004111A1; (15) thiophenylthiopyrane dioxides as described in U.S. Pub. Application No. 2004/0266826A1; (16) lactam derivatives as described in U.S. Pub. Application No. 2004/0266751A1; (17) hydantoin derivatives as described in U.S. Pub. Application No. 2004/0254231A1; (18) pyridine matrix metalloproteinase inhibitors as described in U.S. Pub. Application No. 2004/0209922A1; (19) aromatic sulfone hydroxamic acids as described in U.S. Pub. Application No. 2004/0209914A1; (20) hydantoins and related heterocycles as described in U.S. Pub. Application No. 2004/0209874A1; (21) hydroxamic acid derivatives as described in U.S. Pub. Application No. 2004/0192733A1; (22) arylpiperazines as described in U.S. Pub. Application No. 2004/0171641A1; (23) matrix metalloproteinase inhibitors that (a) bind allosterically to one or more matrix at least the S1' pocket, at least the S1" pocket (as defined) or at least the S1' pocket and the S1" pocket of the matrix metalloproteinase; and (b) exhibit selectivity for one or more matrix metalloproteinase other than MMP-13 as described in U.S. Pub. Application No. 2004/0171543A1; (24) hydroxamic acid and amide compounds as described in U.S. Pub. Application No. 2004/0167182A1; (25) novel Pyrimidine-4,6-dicarboxylic acid diamides as described in U.S. Pub. Application No. 2004/0167120A1; (26) heteroarylsulfonylmethyl hydroxamic acids and amides inhibitors of metalloproteinase as described in U.S. Pub. Application No. 2004/0142979A1; (27) amide and ester matrix metalloproteinase inhibitors as described in U.S. Pub. Application No. 2004/0142950A1; (28) spiro-cyclic beta-amino acid derivatives as described in U.S. Pub. Application No. 2004/0132693A1; (29) substituted biaryl oxobutyric acids as described in U.S. Pub. Application No. 2004/0127500A1; (30) isoxazoline derivatives as described in U.S. Pub. Application No. 2004/0122005A1; (31) aromatic sulfone hydroxamic acids as described in U.S. Pub. Application No. 2004/0110805A1; (32) a synthesized composition containing one or more of zinc ions, calcium ions, rubidium ions and/or potassium ions that effectively modulates the activity of at least MMP-2 and/or MMP-9 in the wound as described in U.S. Pub. Application No. 2004/0105897A1; (33) aromatic sulfonyl alpha-cycloamino hydroxamic acid compounds as described in U.S. Pub. Application No. 2004/0097487A1; (34) 1g(a)-Amino-n-hydroxy-acetamide derivatives as described in U.S. Pub. Application No. 2004/0082630A1; (35) hydantoin derivatives as described in U.S. Pub. Application No. 2004/0067996A1; (36) hydantoin derivatives as described in U.S. Pub. Application No. 2004/0063698A1; (37) 5,6-Fused 3,4-dihydropyrimidine-2-one derivatives as described in U.S. Pub. Application No. 2004/0043986A1; (38) 6,6-Fused heteroaryl derivatives as described in U.S. Pub. Application No. 2004/0043985A1; (39) 3,4-Dihydroquinolin-2-one, 5,6-fused oxazin-3-one, and 5,6-fused thiazin-3-one derivatives as described in U.S. Pub. Application No. 2004/0043984A1; (40) naphthalene derivatives as described in U.S. Pub. Application No. 2004/0043983A1; (41) monocyclic derivatives as described in U.S. Pub. Application No. 2004/0043979A1; (42) chromone derivatives as described in U.S. Pub. Application No. 2004/0038974A1; (43) phthalimide derivatives as described in U.S. Pub. Application No. 2004/0038973A1; (44) azaisoquinoline derivatives as described in U.S. Pub. Application No. 2004/0038961A1; (45) fused tetrahydropyridine derivatives as described in U.S. Pub. Application No. 2004/0038960A1; (46) 3-Isoquinolinone derivatives as described in U.S. Pub. Application No. 2004/0038959A1; (47) 1,6-Fused uracil derivatives as described in U.S. Pub. Application No. 2004/0034009A1; (48) aromatic sulfone hydroxamates as described in U.S. Pub. Application No. 2004/0024024A1; (49) spirobarbituric acid derivatives as described in U.S. Pub. Application No. 2004/0024001A1; (50) tricylic mercaptomethyl-substituted 2,3-dihydro-quinazolin-5-ones and 2,3-dihydro-benzo-[1,2,4]-thiadiazin-5,5-dioxides as described in U.S. Pub. Application No. 2004/0023953A1; (51) aromatic sulfone hydroxamates as described in U.S. Pub. Application No. 2004/0010019A1; and (52) thiazine and oxazine derivatives as described in U.S. Pub. Application No. 2004/0006077A1.

An inhibitor of the invention can be, for example, a compound disclosed in Current Medicinal Chemistry8:425-474 (2001); J. Med. Chem. 41:199-223 (1998); and U.S. Pat. No. 6,818,622, namely compounds such as listed in Table I below:

| Compound Number | Structure |
| --- | --- |
| | Succinate Peptidomimetic Inhibitors of MMPs |
| 1 | 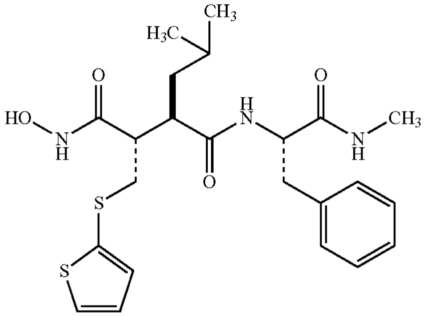<br>Batimastat, BB-94 |
| 2 | 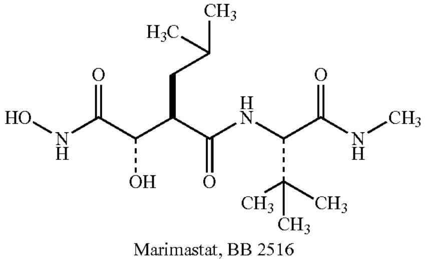<br>Marimastat, BB 2516 |

-continued
| Compound Number | Structure |
|---|---|
| 3 | 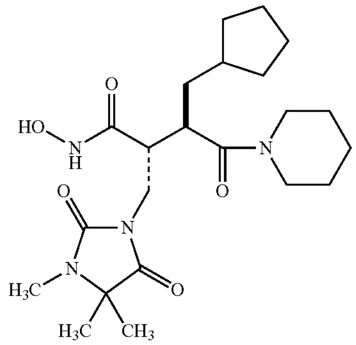 Trocade, Ro 32-3555 |
| 4 | 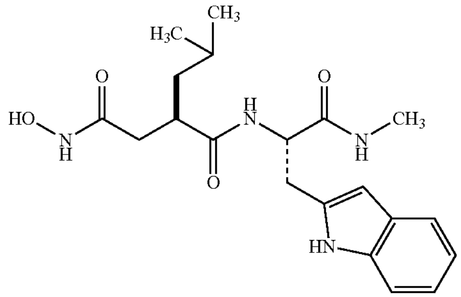 Galardin, Ilomastat, GM6001 |
| 5 | 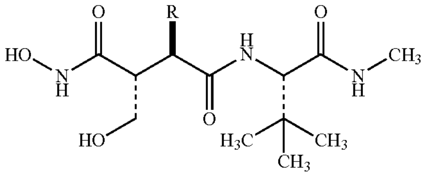 A. R: iso-Butyl<br>B. R: Ph<br>C. R: 4-CH3Ph<br>D. R: 4-OHCH3-Ph |

-continued
| Compound Number | Structure |
|---|---|
| 6 | 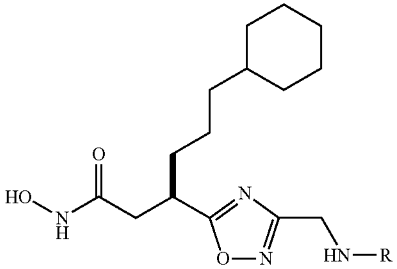<br>A. R: H<br>B. R: —$S(O)_2Ph$<br>C. R: $S(O)_2$(ter-Bu)<br>D. R: —C(O)R1 |
| 7 | 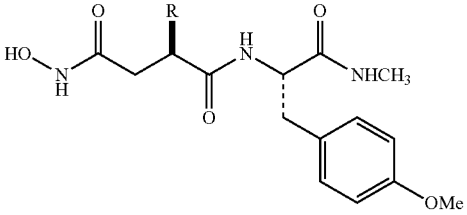<br>A. R: $CH_2CH(CH_3)_3$<br>B. R: $CH_2$(4-OMe)Ph |
| 8 | 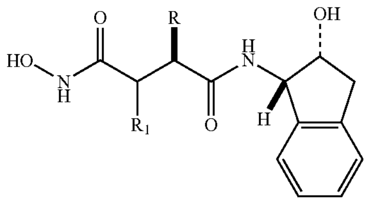<br>A. R1: H; R: OH<br>B. R1: H; R: 4-OMe-Bn<br>C. R1: H; R: 3-OH-Bn<br>D. R1: —$NHCH_2(c\text{-}C_3H_5)$; R: 3-OH-Bn |

-continued
| Compound Number | Structure |
|---|---|
| 9 | 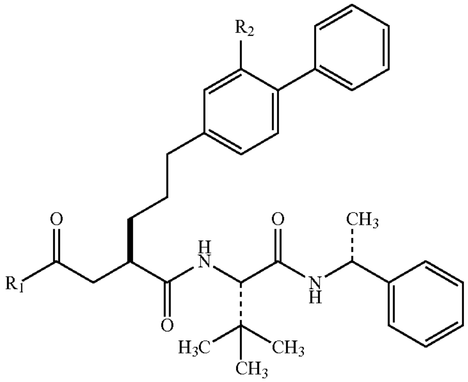 A. R2: $CH_3$; R1: OH<br>B. R2: Cl; R1: —NHOH |
| 10 | 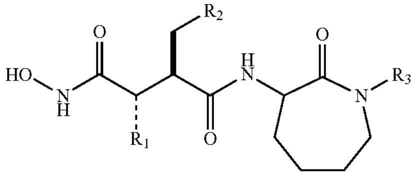 A. R1: H; R2: i-Pr; R3: H<br>B. R1: H; R2: i-Pr; R3: $CH_2CO_2Me$<br>C. R1: H; R2: n-Heptyl; R3: $CH_2CO_2Me$<br>D. R1: Me; R2: n-Heptyl; R3: $CH_2CH_2OCH_3$<br>E. R1: n-Pr, R2: i-Pr, R3: $CH_2CH_2OCH_3$ |
| 11 | 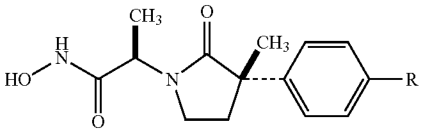 R: H<br>R: $OCH_3$<br>R: benzyoxy<br>R: -3,5-di-MeO-benzyloxy<br>R: -3,5-di-Me-benzyloxy |

-continued
| Compound Number | Structure |
|---|---|
| 12 | 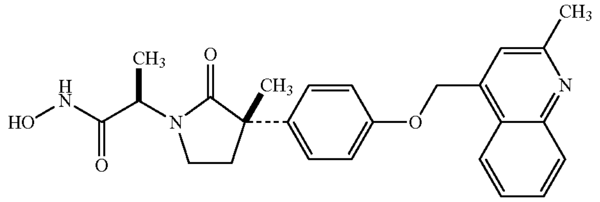 IK682 |
| 13 | 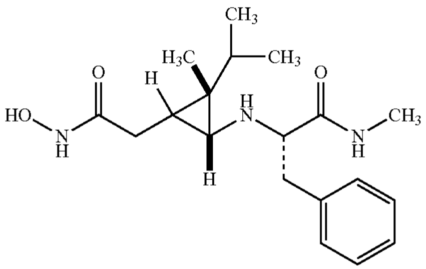 |
| 14 | 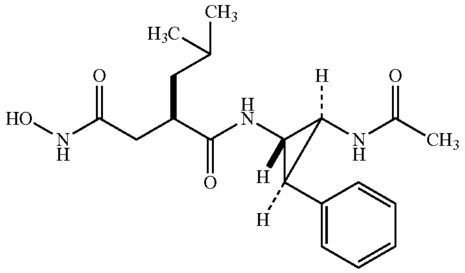 |

-continued
| Compound Number | Structure |
| --- | --- |
| 15 | 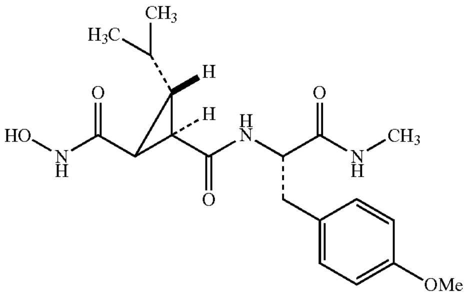 |
| 16 | 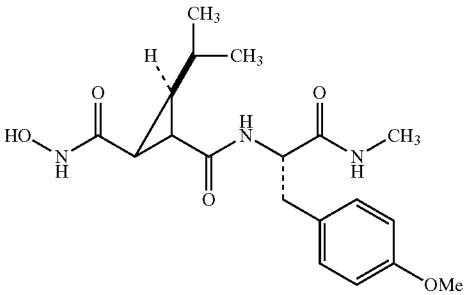 |
| 17 | 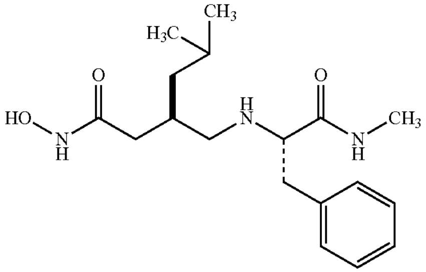 |

-continued
| Compound Number | Structure |
| --- | --- |
| 18 | 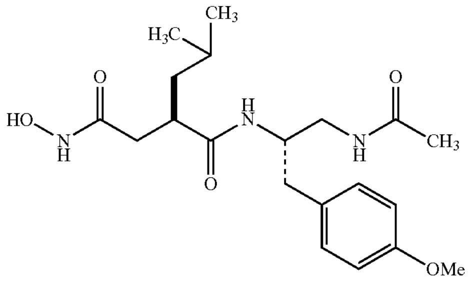 |
| 19 | 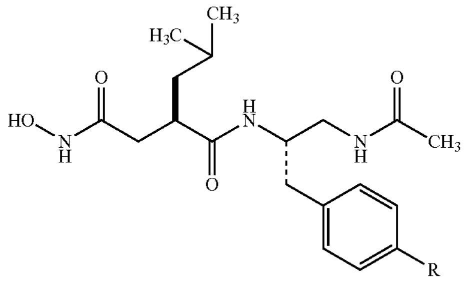 |
| 20 | 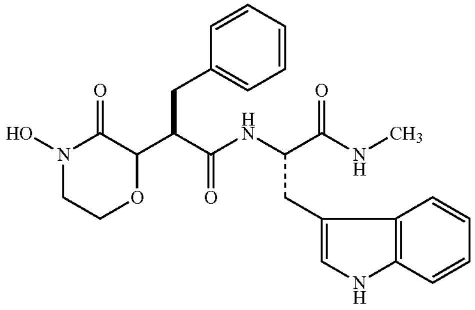 |

-continued
| Compound Number | Structure |
|---|---|
| 21 | 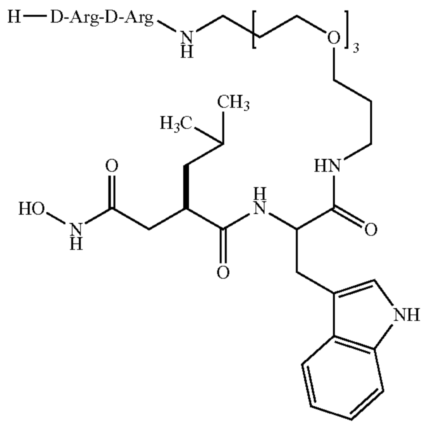 |
| 22 | 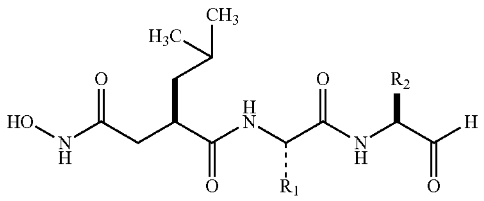<br>A. R1: $CH_2Ph$; R2: $CH_3$<br>B. R1: $CH_2Ph$; R2: $CH_2CH(CH_3)_2$<br>C. R1: $CH_2Ph$; R2: H<br>D. R1: $CH_2CH(CH_3)_2$; R2: $CH_3$ |

-continued
| Compound Number | Structure |
| --- | --- |
| | Succinate Macrocyclic Inhibitors of MMPs |
| 23 | 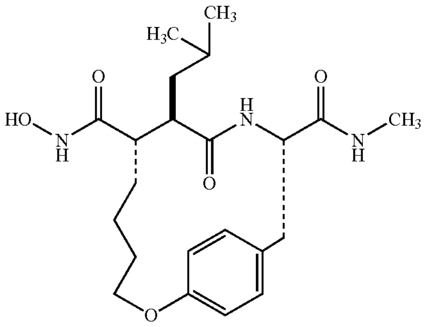 A-177430 |
| 24 | 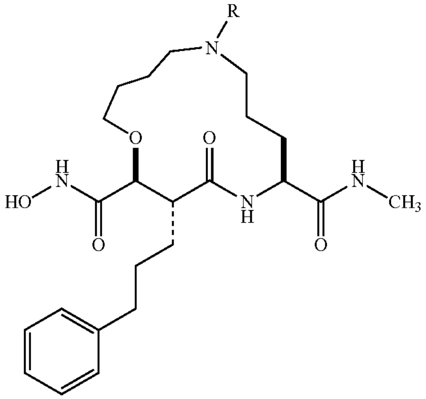 A. R: H<br>B. R: Ac<br>C. R: BOC<br>D. R: $PhSO_2$ |

-continued
| Compound Number | Structure |
|---|---|
| 25 | 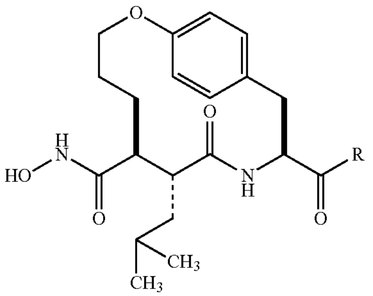<br>R: Gly-$NHCH_3$ |
| 26 | 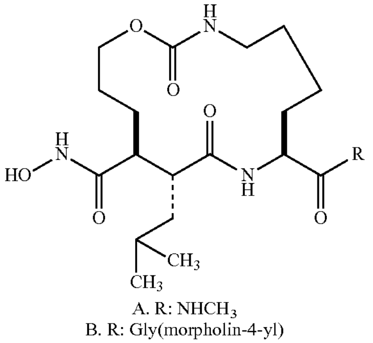<br>A. R: $NHCH_3$<br>B. R: Gly(morpholin-4-yl) |
| 27 | 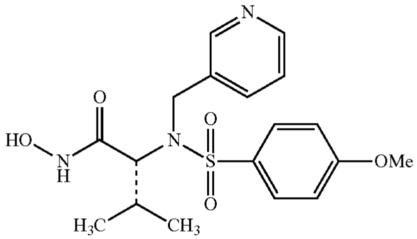 |

-continued
| Compound Number | Structure |
|---|---|
| 28 | 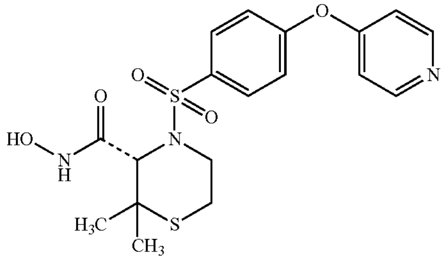 Prinomastat, AG-3340 |
| 29 | 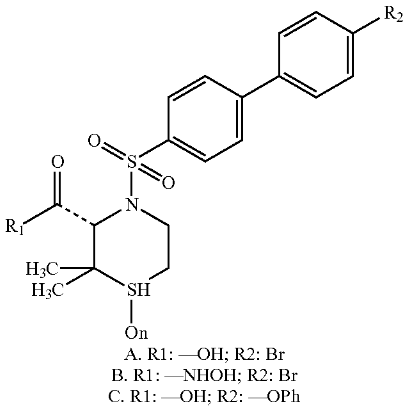 A. R1: —OH; R2: Br<br>B. R1: —NHOH; R2: Br<br>C. R1: —OH; R2: —OPh |
| 30 | 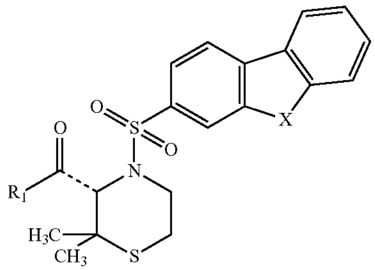 A. R1: —OH; X: OH<br>B. R1: —NHOH; X: O |

-continued
| Compound Number | Structure |
|---|---|
| | C. R1: —NHOH; X: $CH_2$ |
| 31 | 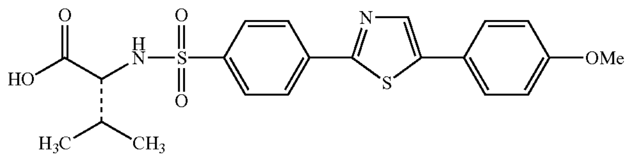 |
| 32 | 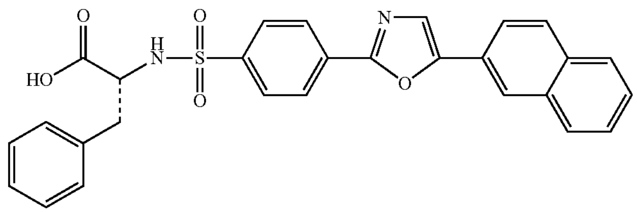 |
| 33 | 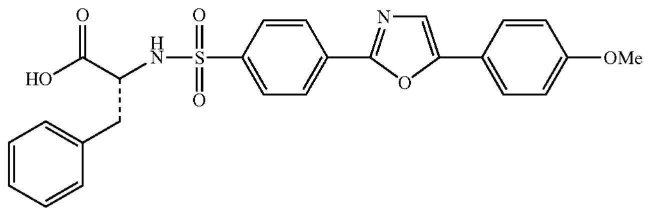 |
| 34 | 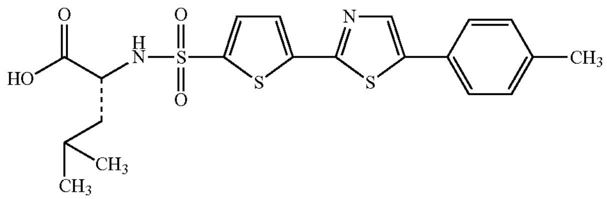 |

-continued
| Compound Number | Structure |
| --- | --- |
| 35 | 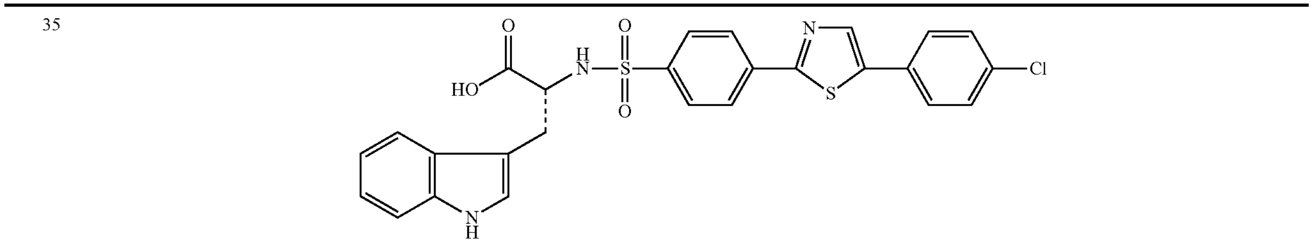 |
| 36 | 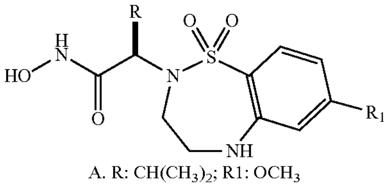 A. R: $CH(CH_3)_2$; R1: $OCH_3$ B. R: Me; R1: Ph C. R: $(CH_2)_4NHSO_2$; R1: $OCH_2Ph$ D. R: $CH_2CH(CH_3)_2$; R1: $OCH_2Ph$ E. R: $CH_3$; R1: $O(3\text{-}NO_2)Ph$ |
| 37 | 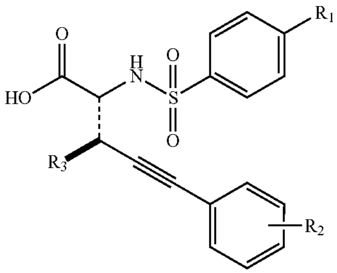 |
| | R1 | R2 | R3 |
| --- | --- | --- | --- |
| a | —O(n-Bu) | H | H |
| b | 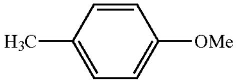 | H | H |

-continued
| Compound Number | | Structure | | |
|---|---|---|---|---|
| | c | 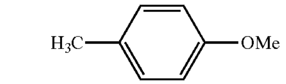 | 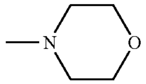 meta | H |
| | d | 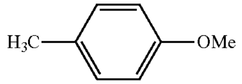 | H | OBn |
| | e | 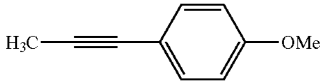 | H | H |
| 38 | | 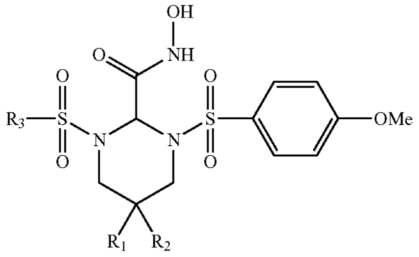 A. R1 = R2: H<br>B. R1 = R2: $CH_3$<br>B. R1 = R2: $-S(CH_2)_3S-$ | | |
| 39 | | 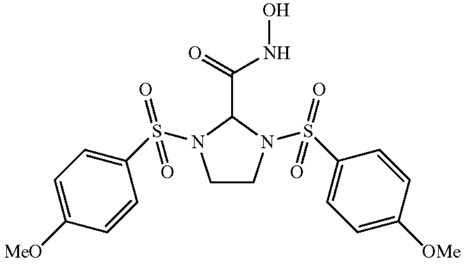 | | |

-continued
| Compound Number | Structure |
|---|---|
| 40 | 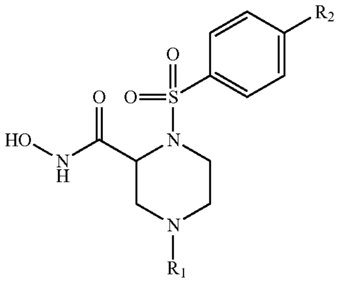<br>A. R1: H; R2: $OCH_3$<br>B. R1: n-$CH_6H_{13}$; R2: $OCH_3$<br>C. R1: Bn; R2: $OCH_3$<br>D. R1: $CH_2CH(CH_3)_2$; R2: $CH_3$ |
| 41 | 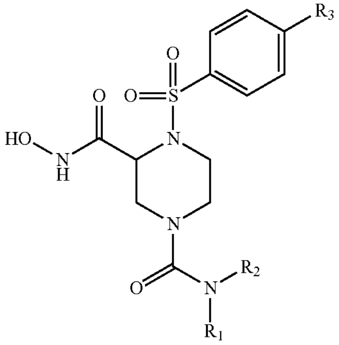<br>A. R1: c-$CH_3H_5CH_3$—; R2: n-Pr; R3: $OCH_3$<br>B. R1 = R2: —$CH_2CH_2N(CH_3)CH_2CH_2$-; R3: $OCH_3$<br>C. R1 = R2: —$(CH_2)_6$; R3: $OCH_3$<br>D. R1 = R2: —$CH_2CH_2OCH_2CH_2$—; R3: $OCH_3$ |

-continued
| Compound Number | Structure |
|---|---|
| 42 | 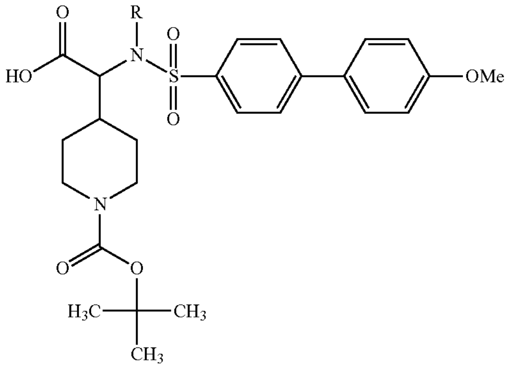 A. (R) R: H B. (S) R: H |
| 43 | 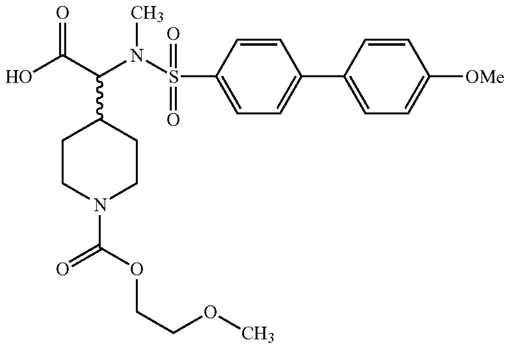 |
| 44 | 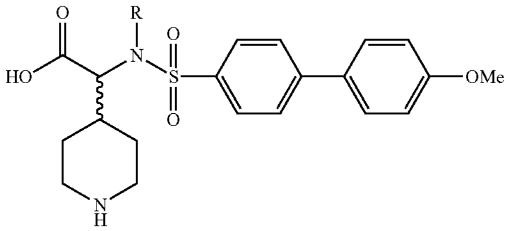 R: H |

-continued
| Compound Number | Structure |
|---|---|
| 45 | 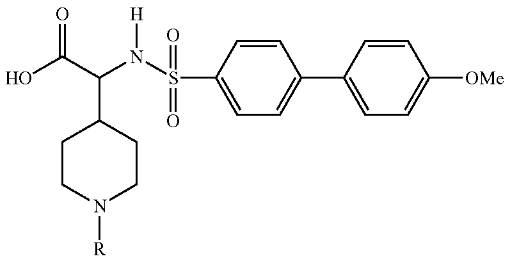 |
| | R |
| | a 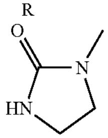 |
| | b 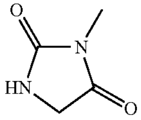 |
| | c 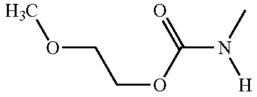 |
| | d 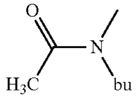 |

-continued
| Compound Number | Structure |
| --- | --- |
| 46 | 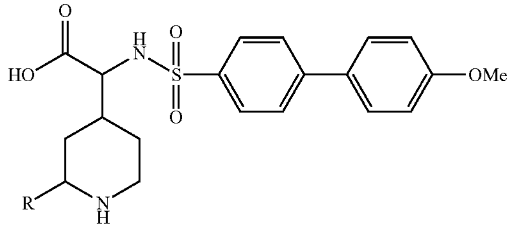<br>A. R: —NHPh<br>B. R: —N(Me)$SO_2$Me<br>C. R: —NO(t-Bu) |
| 47 | 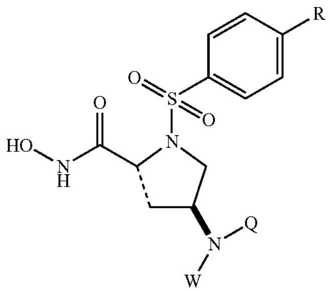<br>A. Q: H; W: H; R: $OCH_3$<br>B. Q: —$(CH_2)_2CH_3$; W: H; $OCH_3$<br>C. Q: —$SO_2CH_3$; W: —$CH_2$-3-$Pyr_2$C; R: $OCH_3$ |
| 48 | 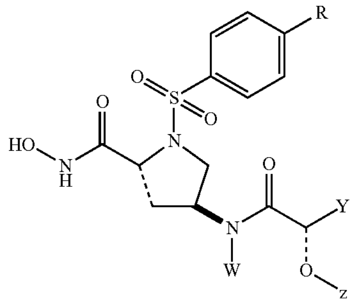<br>A. W: H; Y: $CH_3$; Z: —$CH_2$Ph; R: $OCH_3$<br>B. W: n-Pr; Y: $CH_3$; Z: H; R: $OCH_3$<br>C. H; Y: $CH_3$; Z:: H; R: —O(n-Bu) |

-continued
| Compound Number | Structure |
|---|---|
| 49 | 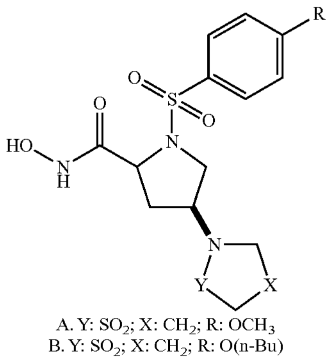 A. Y: $SO_2$; X: $CH_2$; R: $OCH_3$ B. Y: $SO_2$; X: $CH_2$; R: O(n-Bu) |
| 50 | 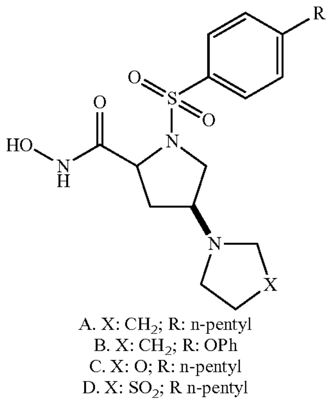 A. X: $CH_2$; R: n-pentyl B. X: $CH_2$; R: OPh C. X: O; R: n-pentyl D. X: $SO_2$; R n-pentyl |

-continued
| Compound Number | Structure |
| --- | --- |
| 51 | 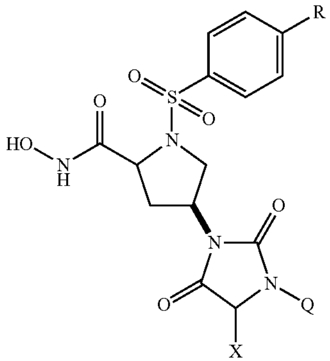<br>A. Q: $CH_3$; X: H; R: —$OCH_2CH_2OCH_3$<br>B. Q: $CH_3$; X: H; R: —OPh<br>C. Q: H; X: —$SCH_3$; R: O(n-Bu)<br>D. Q: —$CH_2CH{=}CH_2$; X: H; R: —$OCH_2CH_2OCH_3$ |
| 52 | 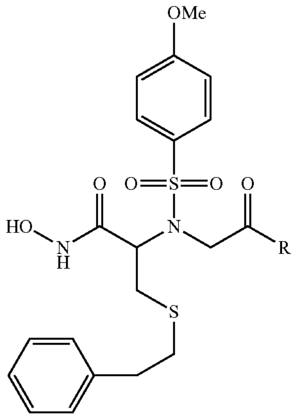<br>A. R: —$NHCH_2$(3-Pyridyl)<br>B. R: —$NHCH_2C_6H_4$-4-(OMe)<br>C. R: —$NHCH_2C_6H_2$-2,4,6-(OMe)<br>D. R: —$N(CH_2CH_2)_2O$ |

-continued
| Compound Number | Structure |
|---|---|
| 53 | 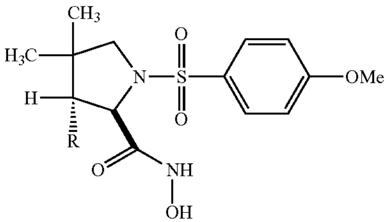<br>A. R: —$CH_2SCH_2Ph$<br>B. R: —$CH_2$═$CH_2$<br>C. R: —$NHCH_2C_6H_2$-2,4,6-(OMe)<br>D. R: —CH(OH)$CH_2SPh$ |
| 54 | 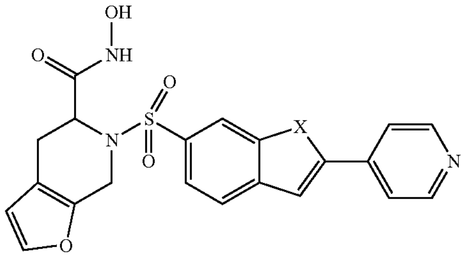<br>X: O; N(R); S |
| 55 | 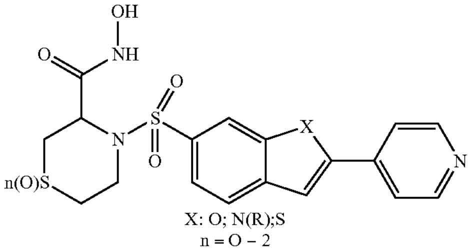<br>X: O; N(R);S<br>n = O − 2 |

-continued
| Compound Number | Structure |
|---|---|
| 56 | 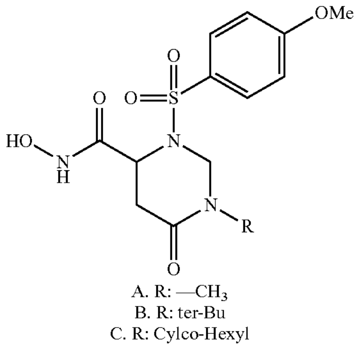<br>A. R: —$CH_3$<br>B. R: ter-Bu<br>C. R: Cylco-Hexyl |
| 57 | 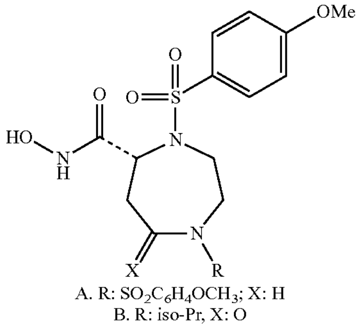<br>A. R: $SO_2C_6H_4OCH_3$; X: H<br>B. R: iso-Pr, X: O |
| 58 | 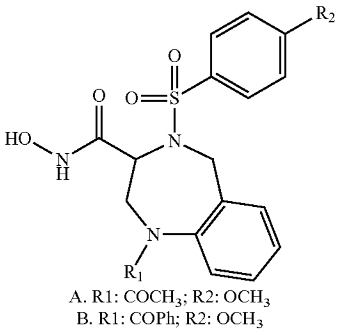<br>A. R1: $COCH_3$; R2: $OCH_3$<br>B. R1: COPh; R2: $OCH_3$ |

-continued
| Compound Number | Structure |
|---|---|
| | C. R1: CO(2-thiophene); R2: $OCH_3$<br>D. R1: CO(p-Biphenyl); R2: $OCH_3$<br>E. R1: $COCH_3$; R2: $OCH_2C{\equiv}CCH_3$ |
| 59 | 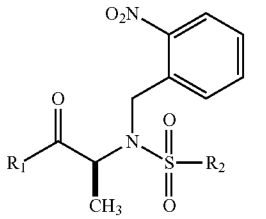<br>A. R1: COOH; R2: $C_6H_5$<br>B. R1: NHOH; R2: $C_6H_5$<br>C. R1: CO(2-thiophene); R2: $OCH_3$<br>D. R1: COOH; R2: 3-$CF_3$—$C_6H_4$<br>E. R1: NHOH; R2: 3-$CF_3$—$C_6H_4$ |
| 60 | 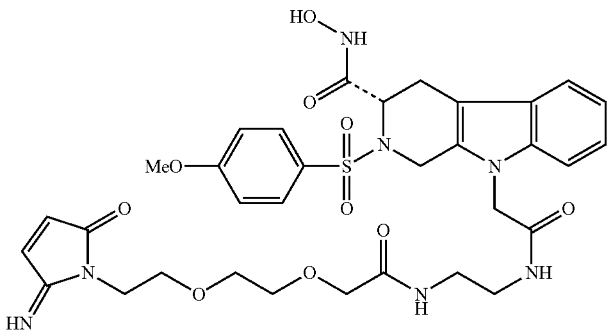 |

-continued
| Compound Number | Structure |
|---|---|
| 61 | 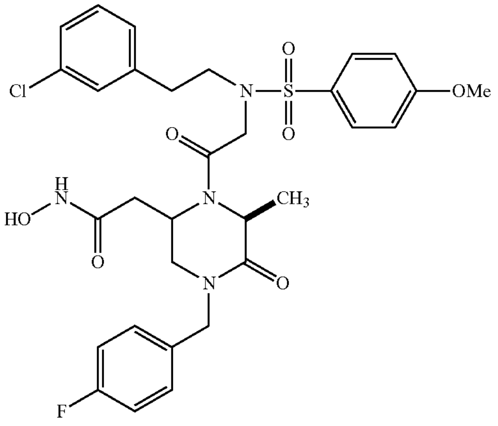 |
| 62 | 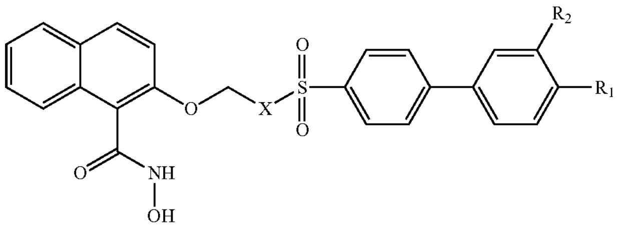 A. X: $CH_2CH_2$; R1: $OCH_3$; R2: H<br>B. X: $CH_2NH$; R1: $OCH_3$; R2: H<br>C. X: $CH_2$; R1: CO(2-thiophene); R2: $OCH_3$<br>D. X:; R1: H; R2: $CH_2CN$ |
| 63 | 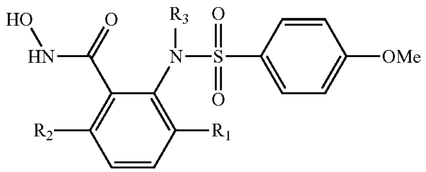 |
| | R1 | R2 | R3 |
|---|---|---|---|
| a | H | H | —$CH_2$Ph |
| b | M | H | —$CH_2$Ph |
| c | H | Me | —$CH_2$Ph |
| d | Me | H | —$CH_2$-3-Py |

-continued
| Compound Number | Structure | | | |
|---|---|---|---|---|
| | e | —$OCH_2CONHOH$ | H | —$CH_2Ph$ |
| | f | —$OC(CH_3)_2CONHOH$ | H | —$CH_2Ph$ |
| | g | —$CO_2CH_3$ | H | —$CH_2$-3-Py |
| 64 | | 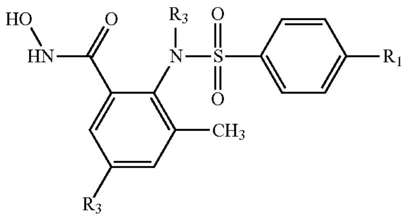 | | |
| | | R1 | R2 | R3 |
| | a | OMe | $CH_2Ph$ | $CH_2NEt_2$ |
| | b | OMe | $CH_2$-3-Py | $NMe_2$ |
| | c | O-4-Py | Me | H |
| | d | Ph-4-OMe | $CH_2$-3-Py | H |
| | e | $OCH_2$-3-Py | Me | Br |
| | f | $O(CH_2)_2Ph$ | $CH_2Ph$ | $CH_3$ |
| 65 | | 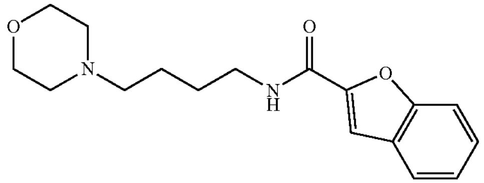 CL-82198 | | |
| 66 | | 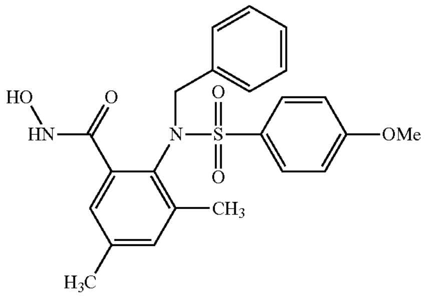 WAY-152177 | | |

-continued
| Compound Number | Structure |
| --- | --- |
| 67 | 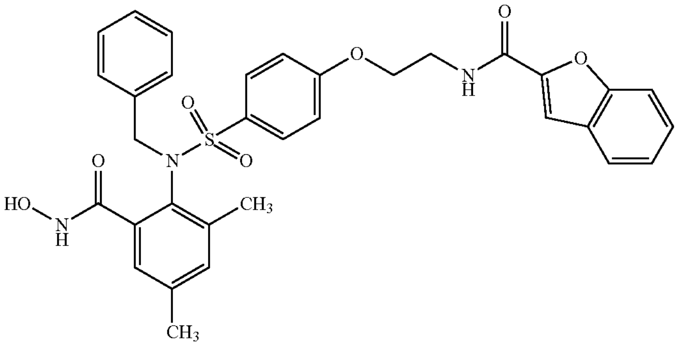 WAY-170523 |
| 68 | 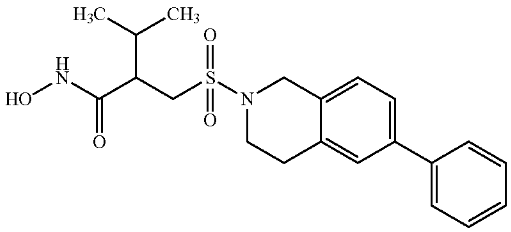 |
| 69 | 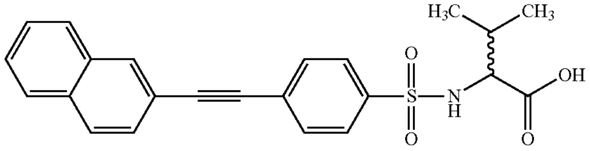 |
| 70 | 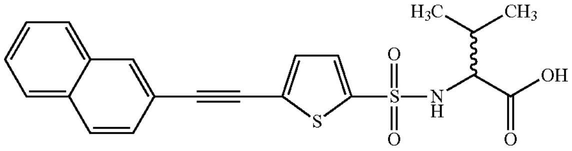 |

-continued
| Compound Number | Structure |
|---|---|
| 71 | 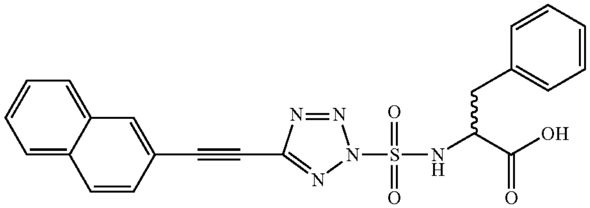 |
| 72 | 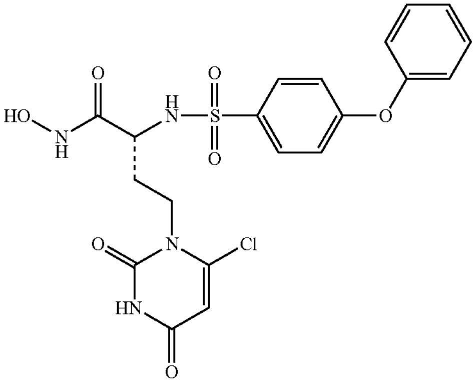 |
| | Sulfone Hydroxamate Inhibitors of MMPs |
| 73 | 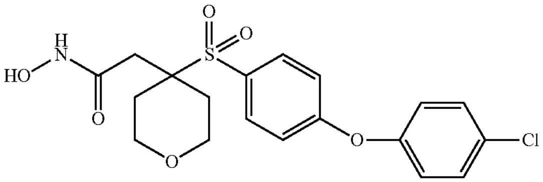 RS-113, 456 |

-continued
| Compound Number | Structure |
|---|---|
| 74 | 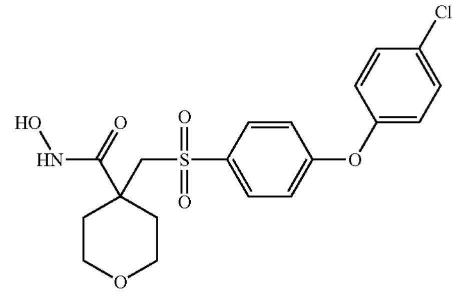<br>RS-130, 830 |
| 75 | 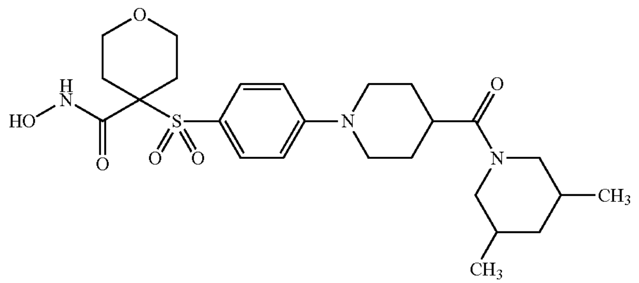 |
| 76 | 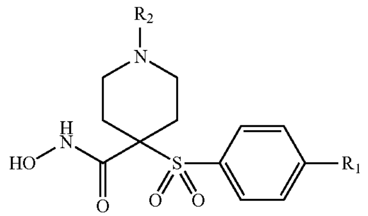 |
| | $R_1$ | $R_2$ |
|---|---|---|
| a | —O-n-butyl | 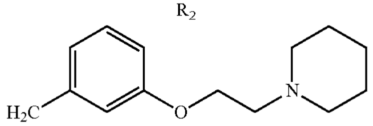 |
| b | —O-(4-chloro)Ph | Ethyl |
| c | —O(4-chloro)Ph | Benzyl |

-continued
| Compound Number | Structure | | |
|---|---|---|---|
| | d | —$OCH_3$ | 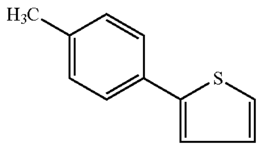 |
| | e | —$OCH_3$ | 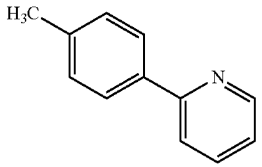 |
| 77 | 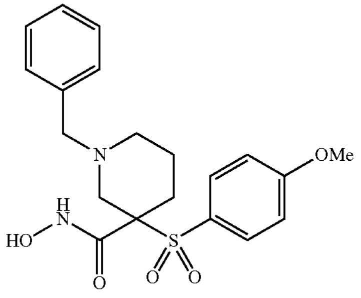 | | |
| 78 | 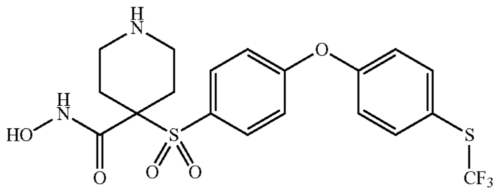 | | |

-continued
| Compound Number | Structure |
|---|---|
| 79 | 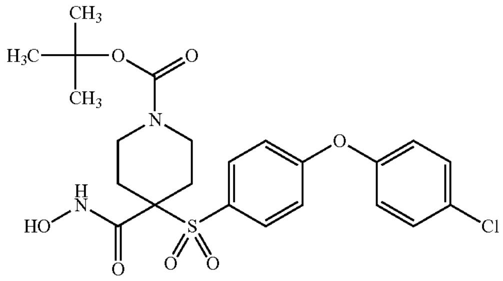 |
| 80 | 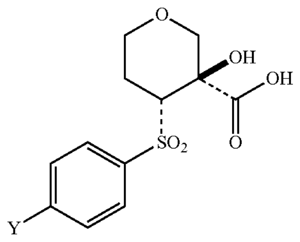 |
| 81 | 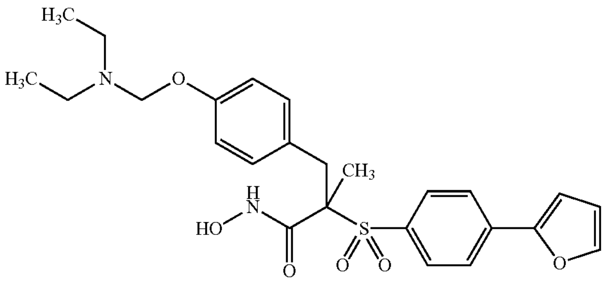 |

-continued
| Compound Number | Structure | | |
|---|---|---|---|
| 82 | 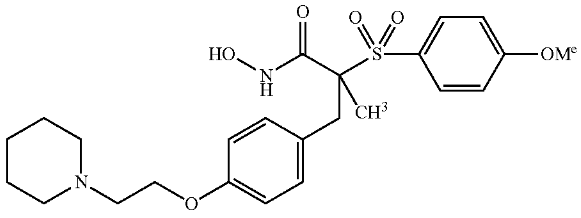 | | |
| 83 | 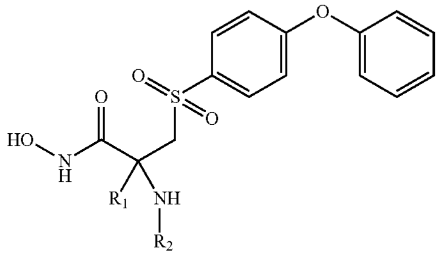 | | |
| | | $R_1$ | $R_2$ |
| | a | $CH_3$ | H |
| | b | $CH_3$ | $CH_2Ph$ |
| | c | $CH_3$ | 2-naphthylmethyl |
| | d | Ph | H |
| 84 | 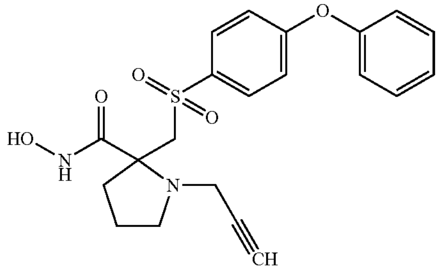 | | |

-continued
| Compound Number | Structure |
|---|---|
| 85 | 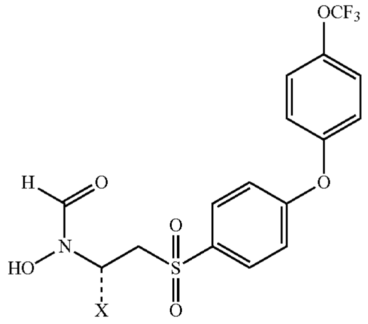 x |
| | a 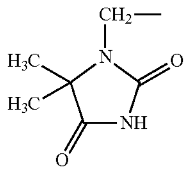 |
| | b 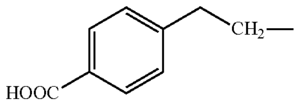 |
| | c 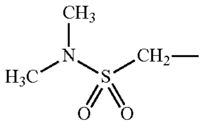 |
| | d 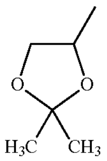 |

-continued
| Compound Number | Structure |
| --- | --- |
| | e 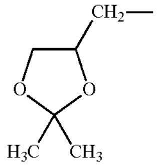 |
| 86 | 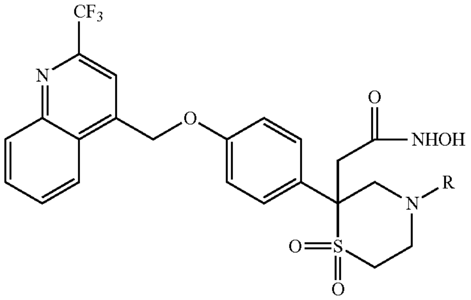 |
| 87 | 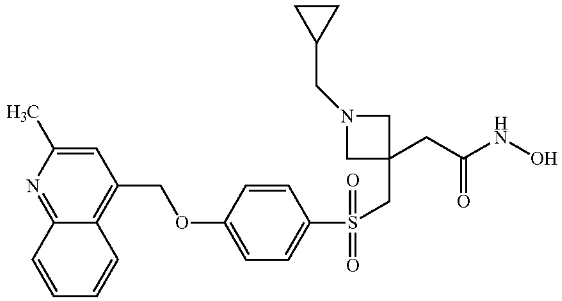 |

-continued
| Compound Number | Structure |
|---|---|
| 88 | 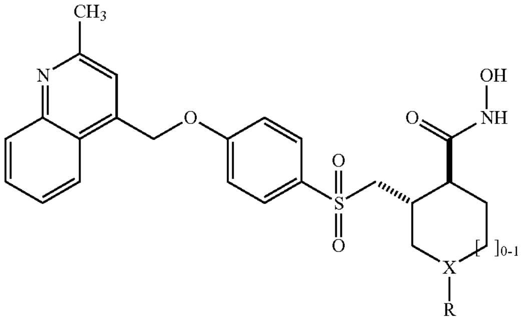 |
| 89 | 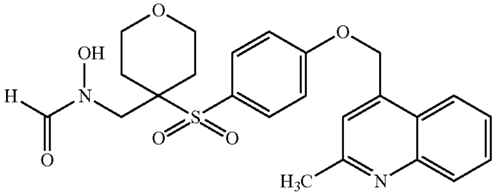 |
| Thiol Inhibitors of MMPs | |
| 90 | 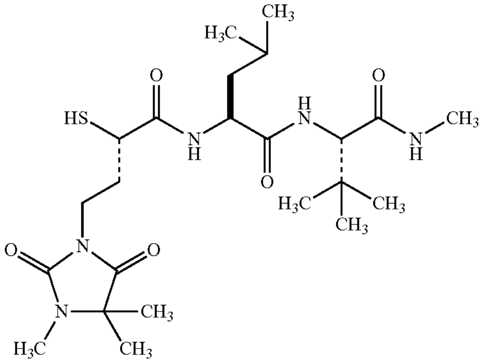<br>D-2163<br>BMS-275, 291 |

-continued
| Compound Number | Structure |
| --- | --- |
| 91 | 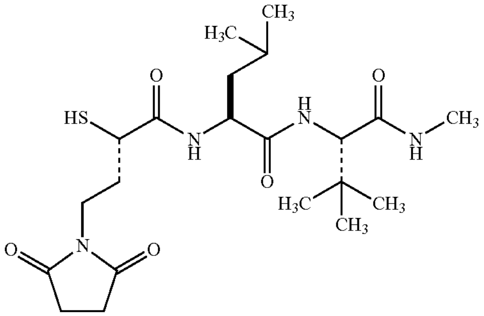 D-1927 |
| 92 | 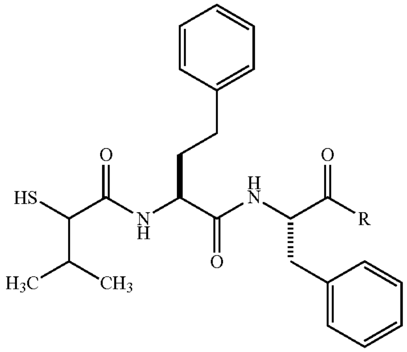 R: OH<br>R: $NHCH_3$ |
| 93 | 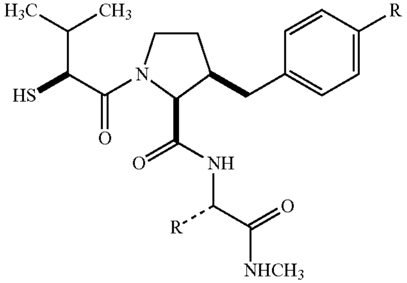 |

-continued
| Compound Number | Structure |
|---|---|
| 94 | R: —$CH_2$(4-OH-Ph)<br>R: —$C(CH_3)_3$<br>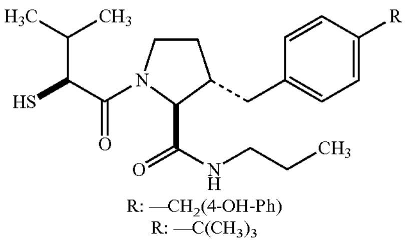<br>R: —$CH_2$(4-OH-Ph)<br>R: —$C(CH_3)_3$ |
| 95 | 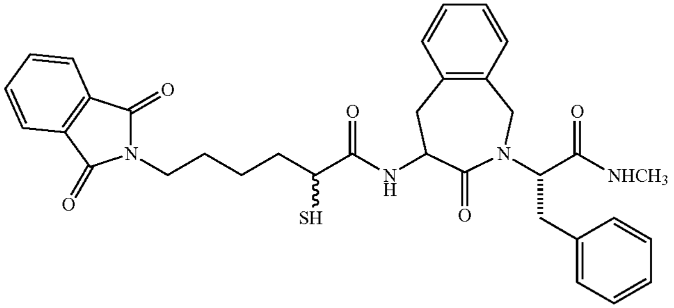 |
| 96 | 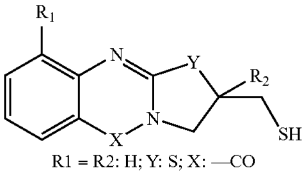<br>R1 = R2: H; Y: S; X: —CO |

-continued
| Compound Number | Structure |
|---|---|
| 97 | 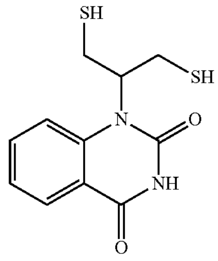 |
| | Reverse Hydroxamic Acid Inhibitors of MMPs |
| 98 | $P_1'$ $P_3'$ 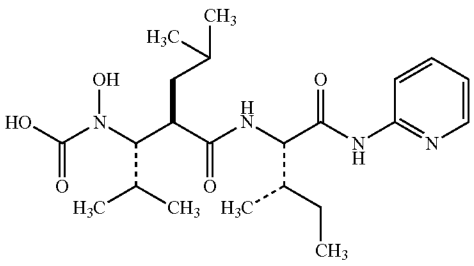 $P_1'$-alpha $P_2'$ GW-3333 |
| 99 | 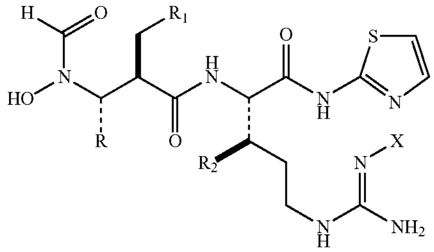 a: R = n-Pr; $R_1$ = $CH(CH_3)_2$; $R_2$ = H; X = $NO_2$<br>b: R = c-Pr; $R_1$ = c-hexyl; $R_2$ = H; X = $NO_2$<br>c: R = $CH_2CH_2CF_3$; $R_1$ = c-hexyl; $R_2$ = H; X = $NO_2$<br>d: R = $CH_2CH_2CH_3$; $R_1$ = $CH(CH_3)_2$; $R_2$ = H; X = $—SO_2CH_3$<br>e: R = $CH_2CH_2CH_3$; $R_1$ = 2-(5-methylthienyl); $R_2$ = H; X = -2-pyridylsulfonyl |

-continued
| Compound Number | Structure |
|---|---|
| | f: R = $CH_2CH_2CF_3$; $R_1$ = $CH(CH_3)_2$; $R_2$ = $CH_3$; X = —$SO_2CH_3$<br>g: R = $CH_3$; $R_1$ = $CH(CH_3)_2$; $R_2$ = $CH_3$; X = $NO_2$ |
| 100 | 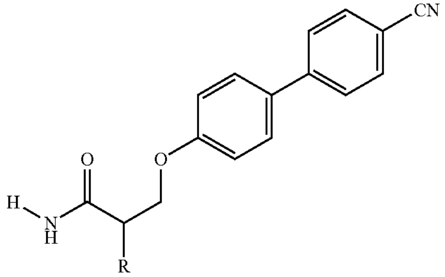<br>R: H<br>R: CH |
| 101 | 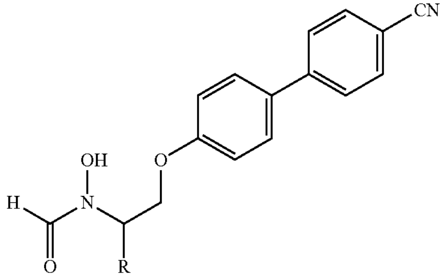 |
| | R |
|---|---|
| a | —H |
| b | Me |
| c | 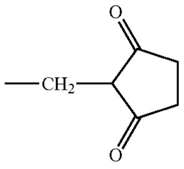 |

-continued
| Compound Number | Structure |
|---|---|
| d | 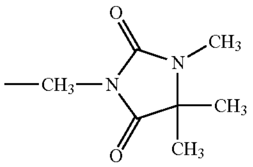 |
| e | 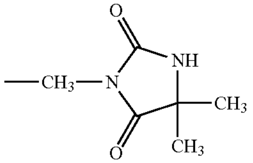 |
| f | 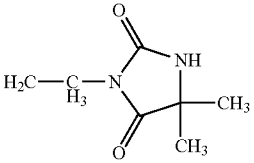 |
Phosphorus-Based Inhibitors of MMPs
102
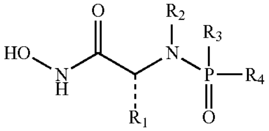
| | $R_1$ | $R_2$ | $R_3$ | $R_4$ |
|---|---|---|---|---|
| a | H | $—CH_2CH_2Ph$ | $—CH_3$ | -Ph |
| b | $—CH_3$ | $—CH_2Ph$ | $—CH_3$ | -Ph |
| c | $—CH_3$ | $-n-C_6H_{13}$ | $—CH_3$ | -Ph |
| (R)-d | $—CH_2CH(CH_3)_2$ | H | $—CH_3$ | -Ph |
| (S)-e | $—CH_2CH(CH_3)_2$ | H | $—CH_3$ | -Ph |
| (R)-f | $—CH_2CH(CH_3)_2$ | $—CH_2Ph$ | $—CH_3$ | -Ph |
| (S)-g | $—CH_2CH(CH_3)_2$ | $—CH_2Ph$ | $—CH_3$ | -Ph |
| h | $—CH_2CH(CH_3)_2$ | $—CH_2Ph$ | -Ph | -Ph |
| i | $—CH_2CH(CH_3)_2$ | $—CH_2Ph$ | $—CH_3$ | $—CH_3$ |

-continued
| Compound Number | | Structure |
|---|---|---|
| 103 | | 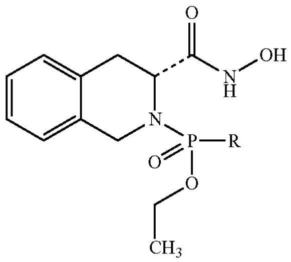 |
| | | R |
| | a | 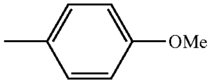 |
| | b | p-pyridyl |
| | c | p-biphenyl |
| | d | 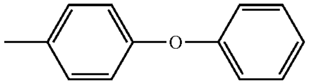 |
| | e | 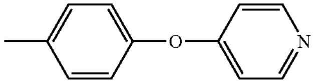 |
| | f | 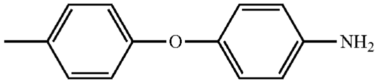 |
| | g | 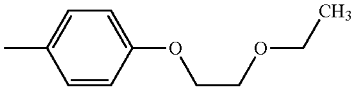 |

-continued
| Compound Number | Structure |
| --- | --- |
| 104 | 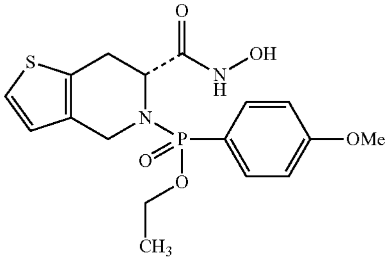 |
| 105 | 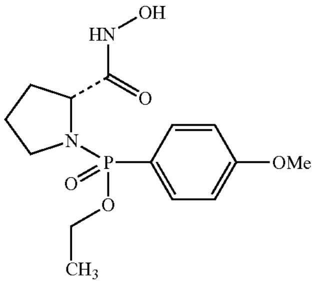 |
| 106 | 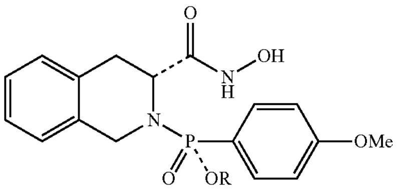 |
| | R |
| --- | --- |
| a | Et |
| b | $CH_2CH_2F$ |
| c | $CH_2CHF_2$ |
| d | $CH_2CF_3$ |
| e | $CH_2CH_2CF_3$ |

-continued

| Compound Number | Structure |
| --- | --- |
| 107 | 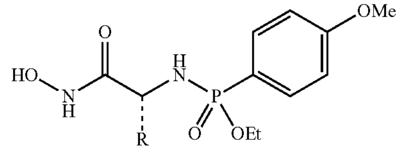<br>THI = Tetrahydroisoquinoline |

| | R |
| --- | --- |
| (3R,R)-a | THI |
| (3R,S)-b | THI |
| (R,R)-a | —$CH_2CH(CH_3)_2$ |
| (R,S)-b | —$CH_2CH(CH_3)_2$ |
| (R,R)-c | —$CH_2CH_2C(O)NHCH_2CH_2Ph$ |
| (R,S)-d | —$CH_2CH_2C(O)NHCH_2CH_2Ph$ |

| Compound Number | Structure |
| --- | --- |
| 108 | 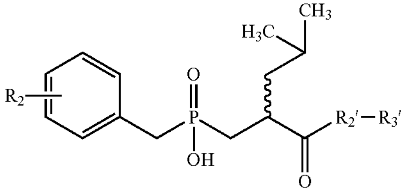<br>Tle = (S)-tert-Leucine |

| | $R_2$ | $R_2'$—$R_3'$ |
| --- | --- | --- |
| a | 4-$PhCH_2$— | —TyrNHMe |
| b | 3-$PhCH_2CH_2$— | —TyrNHMe |
| c | 4-$PhCH_2$— | —TleNHMe |
| d | cyclobutyl$CH_2$— | —TleNHMe |
| e | $PhCH_2CH_2$— | —TleNHMe |
| f | $PhO(CH_2)_4$— | —TleNHMe |

| Compound Number | Structure |
| --- | --- |
| 109 | 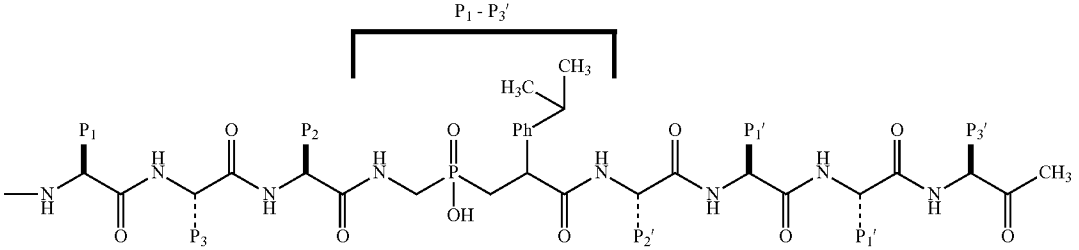 |

a: $P_4$ = Y; $P_3$ = 1; $P_2$ = Y; $P_2'$ = T; $P_3'$ = M; $P_4'$ = P; $P_5'$ = G
b: $P_4$ = L; $P_3$ = 1P $P_2$ = Y; $P_2'$ = Y; $P_3'$ = A; $P_4'$ = P; $P_5'$ = G
c: $P_4$ = L; $P_3$ = M; $P_2$ = Y; $P_2'$ = Y; $P_3'$ = L; $P_4'$ = P; $P_5'$ = G

-continued
| Compound Number | Structure |
|---|---|
| 110 | 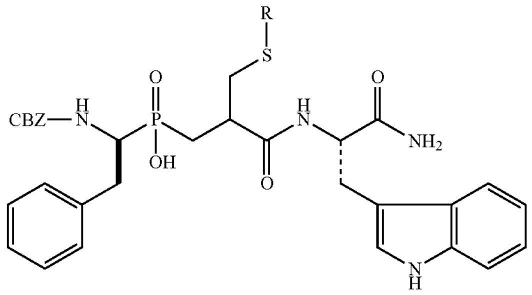 R: —$CH_2$Ph(4-OMe)<br>R: —β-naphtyl |
| 111 | 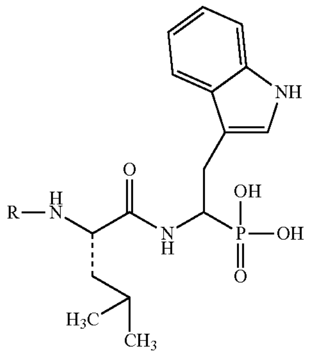 a: R = Prolinyl<br>b: R = 2-furamide<br>c: R = Pyrrole-2-carboxaldehyde |

-continued
| Compound Number | Structure |
| --- | --- |
| | Miscellaneous Inhibitors of MMPs |
| 112 | 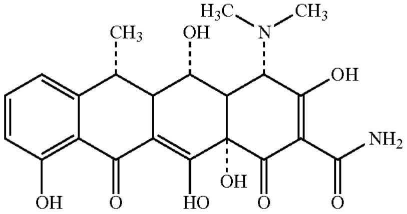 Periostat ® (doxycycline hyclate) |
| 113 | 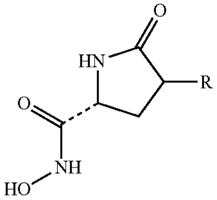 cis-a; R = -(p-PhOMe)<br>cis-b; R = -p-Ph-O[p-(F)Ph]<br>cis-c; R = -p-Ph-p-(F)Ph<br>trans-d; R = p-Ph-O[p-(F)Ph] |
| 114 | 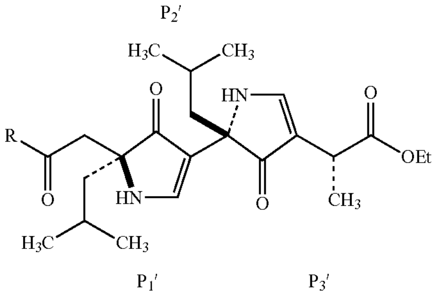 R: NHOH<br>R: OH |

-continued
| Compound Number | Structure |
|---|---|
| 115 | 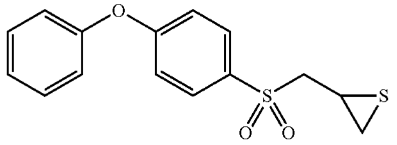 |
| 116 | 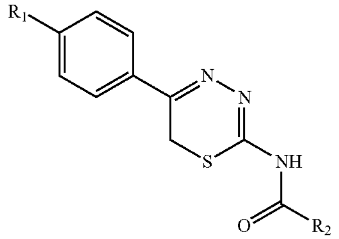<br>a: $R_1$ = H; $R_3$ = dihydroorotic<br>b: $R_1$ = -Ph-4-Cl; $R_2$ = —$SO_2Ph$<br>c: $R_1$ = -Ph-4-$OCH_3$; $R_2$ = —$SO_2Ph$<br>d: $R_1$ = -Ph-4-(5-Cl-thienyl); $R_2$ = —$SO_2Ph$<br>e: $R_1$ = -Ph-4-Cl; $R_2$ = —$SO_2CH_2Ph$<br>f: $R_1$ = -Ph-4-Cl; $R_3$ = —$SO_2$(2-thienyl) |
| 117 | 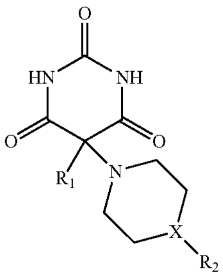 |
| | $R_1$ | $R_2$ | X |
|---|---|---|---|
| a | Ph | $HOCH_2CH_2$— | C |
| b | Ph | 4-$NO_2$-Ph- | N |
| c | n-$C_8H_{17}$ | $HOCH_2CH_2$— | N |
| d | n-$C_8H_{17}$ | 4-$NO_2$-Ph- | N |
| e | 4-biphenyl | 4-$NO_2$-Ph- | N |

-continued
| Compound Number | Structure | | |
|---|---|---|---|
| 118 | 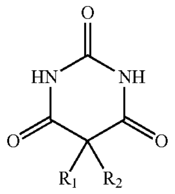 | | |
| | | $R_1$ | $R_2$ |
| | a | n-hexyl | Ph |
| | b | n-hexyl | 4-Ph-Ph- |
| | c | Me | -Ph-O-Ph |
| | d | n-hexyl | -Ph-O-Ph |
| | e | $—CH_2OCH_2Ph$ | -Ph-O-Ph |
| 119 | 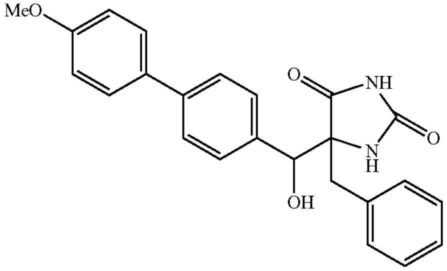 | | |
| 120 | 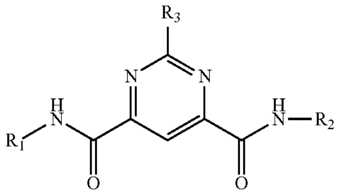 | | |
| 121 | 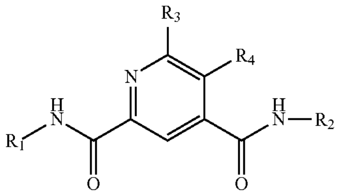 | | |

-continued
| Compound Number | Structure |
|---|---|
| | a: $R_1 = R_2 = 3\text{-}(OCH_3)Bn$; $R_3 = R_4 = H$<br>b: $R_1 = R_2 = 2,4\text{-}(OCH_3)_2Bn$; $R_3 = R_4 = H$<br>c: $R_1 = R_2 = 3\text{-Cl-4-F-Bn}$; $R_3 = R_4 = H$ |
| 122 | 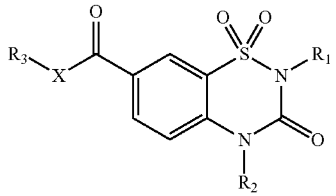<br>a: $R_1 = CH_2Ph$; $R_2 = CH_3$; $R_3 = CH_2(4\text{-}OCH_3)Ph$; X = NH<br>b: $R_1 = CH_2(4\text{-}COOH)Ph$; $R_2 = CH_3$; $R_3 = CH_2Ph$; X = NH<br>c: $R_1 = CH_2Ph$; $R_2 = CH_3$; $R_3 = CH_2Ph$; X = O |
| 123 | 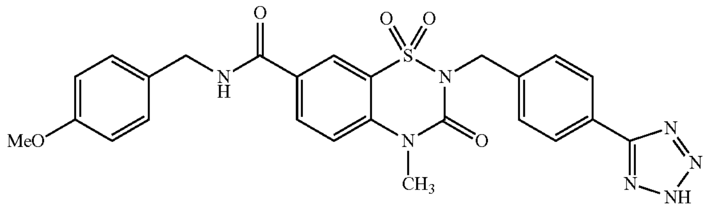 |
| 124 | 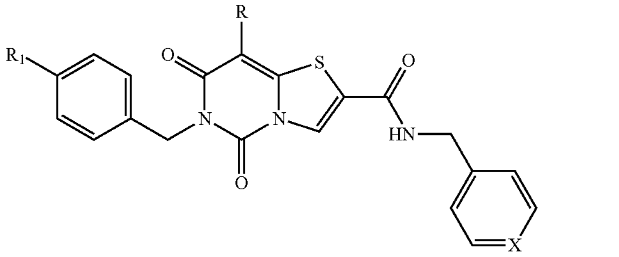<br>a: R = H; $R_1$ = H; X = C<br>b: R = $CH_3$; $R_1$ = H; X = C<br>c: R = $CH_3$; $R_1 = MeO_2S$—; X = N |

-continued
| Compound Number | Structure |
|---|---|
| 125 | 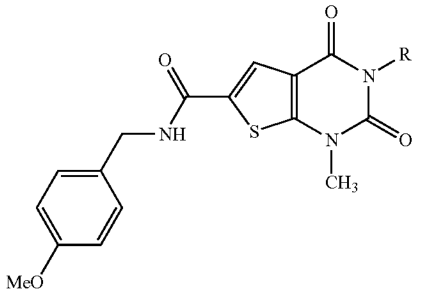<br>a: R = —$CH_2CH$=$CHCH_2CH_3$<br>b: R = —$CH_2C$≡$CCH_2CH_3$<br>c: R = —$CH_2CH_2O$(4-Br)Ph |
| 126 | 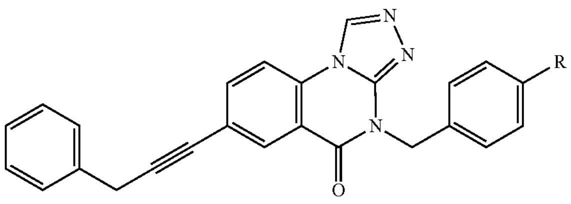<br>a: R = H<br>b: R = —$COOCH_3$<br>c: R = —COOH |
| 127 | 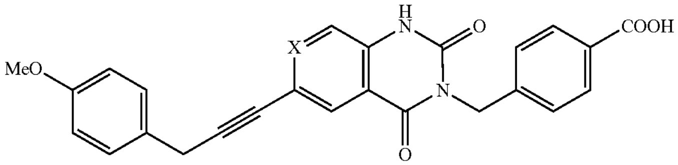<br>a: X = C<br>b: X = N |

-continued
| Compound Number | Structure |
| --- | --- |
| 128 | 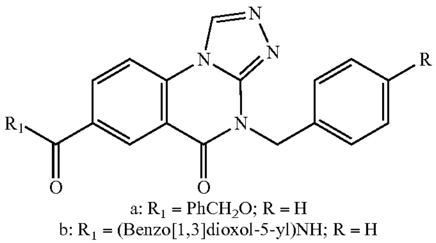<br>a: $R_1$ = $PhCH_2O$; R = H<br>b: $R_1$ = (Benzo[1,3]dioxol-5-yl)NH; R = H |
| 129 | 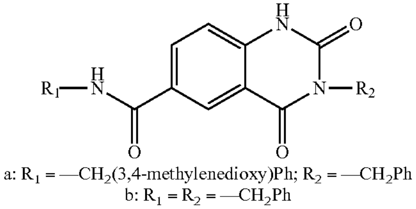<br>a: $R_1$ = —$CH_2$(3,4-methylenedioxy)Ph; $R_2$ = —$CH_2Ph$<br>b: $R_1$ = $R_2$ = —$CH_2Ph$ |
| 130 | 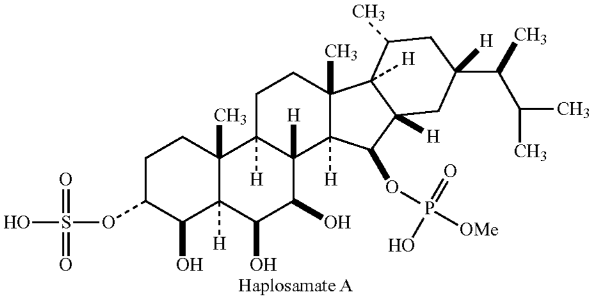<br>Haplosamate A |

-continued
| Compound Number | Structure |
|---|---|
| 131 | 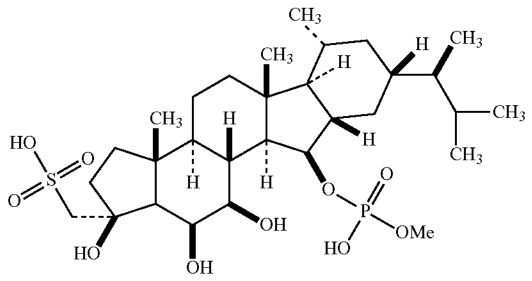 |
| 132 | 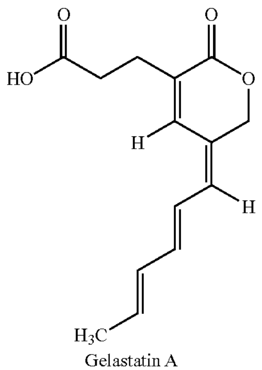<br>Gelastatin A |
| 133 | 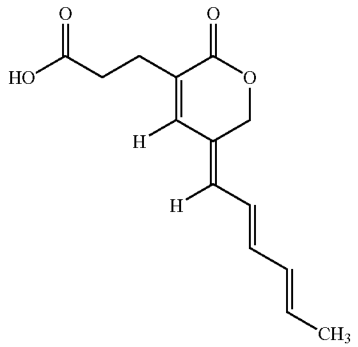<br>Gelastatin B |

-continued
| Compound Number | Structure |
|---|---|
| 134 | 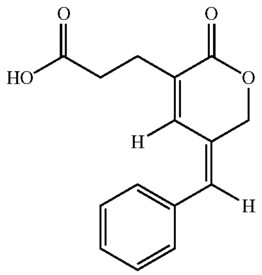 |
| 135 | 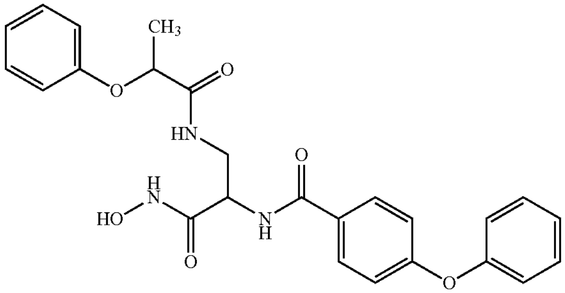 |
Ketone Inhibitors of MMPs
| | |
|---|---|
| 136 | 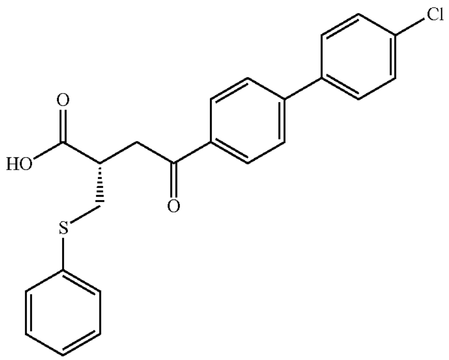 Bay-12-9566 |

-continued
| Compound Number | Structure |
| --- | --- |
| 137 | Tanomastat 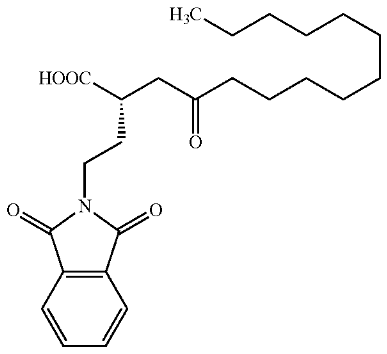 |
| 138 | 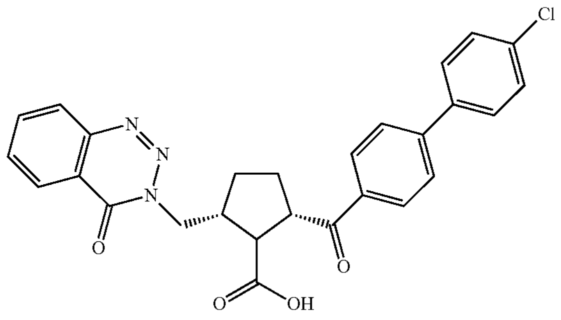 |
| 139 | 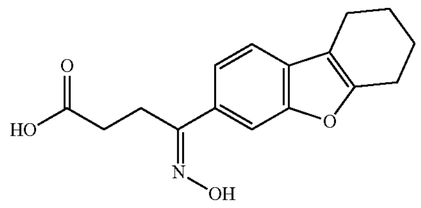 |

-continued
| Compound Number | Structure |
|---|---|
| 140 | 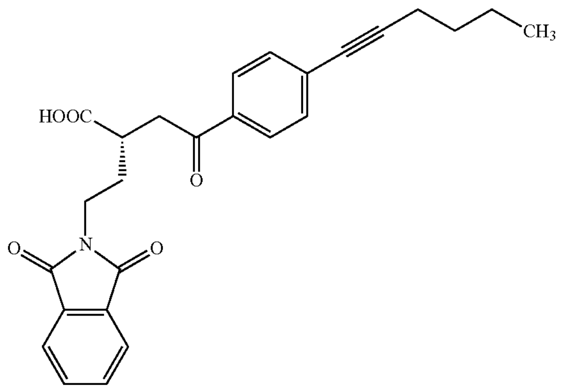 |
| 141 | 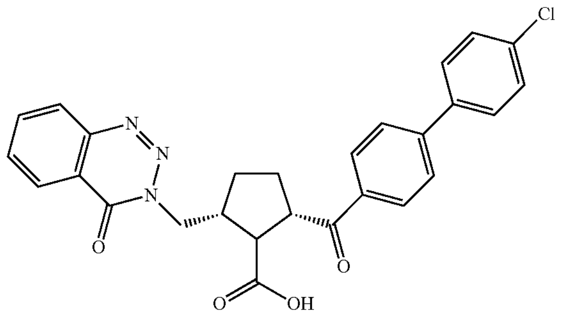 |
| 142 | 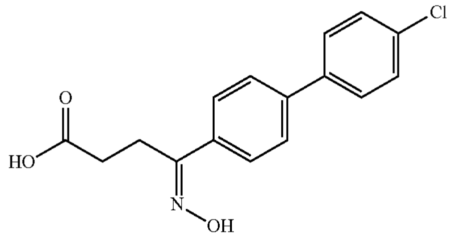 |

-continued
| Compound Number | Structure |
| --- | --- |
| 143 | 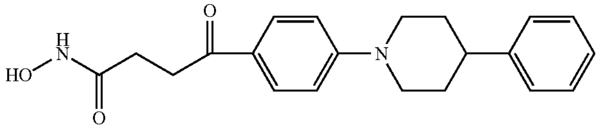 |

As disclosed in U.S. Pat. No. 6,818,622, an inhibitor of the invention can be, without limitation:

2S-[4-(2,5-dioxopyrrolidin-1-yl)-2S-mercaptobutyrylamino]-4-methylpentanoic acid(2,2-dimethyl-1S-methylcarbamoylpropyl)amide; and 2S-[2S-mercapto-4-(3,4,4-trimethyl-2,5-dioxolmidazolidin-1-yl)butyrylamino]-4-methylpentanoic acid(2,2-dimethyl-1S-methylcarbamoylpropyl)amide.

An inhibitor of the invention may be a furin inhibitor such as the peptide inhibitors disclosed by Rockwell et al., Chem. Rev. 102:4525-48 (2002); Tao et al. Febs J. 273:3907-14 (2006); Han et al., Febs J. 273:4459-69 (2006); Stieneke-Grober et al., Embo. J. 11:2407-14 (1992); Hallenberger et al., Nature 360:358-61 (1992); Liu et al., FEBS Lett 556:116-120 (2004); and Kacprzak et al., J. Biol. Chem. 36788-94 (2004).

Additional inhibitors of the invention include: (1)TACE inhibitors described in the following: patent and patent application nos. 20060252778, 20060252832, 20060247231, 20060211730, 20060205797, WO 99/18074, WO 99/65867, U.S. Pat. No. 6,225,311, WO 00/00465, WO 00/09485, WO 98/38179, WO 02/18326 and WO 02/096426, as well as Cherney et al., Bioorg Med Chem Lett 16:1028-1031 (2006), Cherney et al., J Med Chem 46:1811-1823 (2003), Trifilieff et al., J Pharmacol 135:1655-1664 (2002), Wang et al. Mol Pharmacol 65:890-896 (2004), and Le et al., Current Medicinal Chemistry, 2005, 12, 2963-2977; also, the Le et al. reference discloses caspase-1 inhibitors which are useful protease inhibitors according to the present invention; (2) the ADAM10 inhibitors described in publication no. 20060199820; (3) the multicyclic bis-amide MMP inhibitors described in publication no. 20060173183; (4) the sulphonylpiperidine derivatives containing an aryl or heteroaryl group for use as matrix metalloproteinase inhibitors described in publication no. 20060173041; (5) the alkynyl-containing tryptophan derivative inhibitors of tace/matrix metalloproteinase described in publication no. 20060160884; (6) the N-sulfonylpiperidines as metalloproteinase inhibitors (tace) described in publication 20060142336; (7) the hydroxamic acid derivatives as metalloprotease inhibitors described in publication no. 20050250789; the (8) metalloproteinase inhibitors described in publication no. 20050250693; (9) the 2,5-Dioxoimidazolidin-4-yl acetamides and analogues as inhibitors of
metalloproteinase mmp12 described in publication no. 20050245586; (10) the TACE inhibitors described in publication no. 20050215549; (11) the ortho-sulfonamido aryl hydroxamic acids as matrix metalloproteinase inhibitors described in publication no. 20050085504; (12) the substituted 1,3-dihydro-imidazol-2-one and 1,3-dihydro-imidazol-2-thione derivatives as inhibitors of matrix metalloproteinases and/or TNF-alpha converting enzyme (TACE) described in publication no. 20050075384; (13) the sulfamato hydroxamic acid metalloprotease inhibitor described in publication no. 20050049280; (14) the matrix metalloproteinase inhibitors described in publication no. 20050047999; (15) the novel metalloproteinase inhibitors described in publication no. 20050026990; the matrix metalloproteinase inhibitors described in publication no. 20050025702; (16) the hydroxamic and carboxylic acid derivatives described in publication no. 20040176362; (17) the arylpiperazines described in publication no. 20040171641; (18) the matrix metalloproteinase inhibitors described in publication no. 20040171543; (19) the metalloproteinase inhibitors described in publication no. 20040147573; (20) the amide and ester matrix metalloproteinase inhibitors described in publication no. 20040142950; (21) the metalloproteinase inhibitors described in publication nos. 20040138276 and 20040127528; (22) the furin-like protease inhibitors described in publication no. 20040127396; (23) the metalloproteinase inhibitors described in publication nos. 20040116486; 20040110809; and 20040106659; (24) the fused bicyclic metalloproteinase inhibitors described in publication no. 20040034054; (25) the hydroxamic and carboxylic acid derivatives described in publication no. 2003036416; (26) the barbituric acid derivatives described in publication no. 20030229084; and (27) the sultam hydroxamates described in Cherney et al., J. Med. Chem. 47:2981-83 (2004), all of which are incorporated herein in their entirety.

An inhibitor of the invention may be an oligopeptide having from four to ten amino acid units in its sequence or a derivative of such a peptide. The sequence of the oligopeptide may mimic the active site region of TIMP-2 or TIMP-3 or the sequence of proteinase substrate, e.g. syndecan-3, or a sequence otherwise capable of blocking the activity of said proteinase, e.g., capable of inhibiting cleavage of endogenous syndecan-3. Thus, the oligopeptide can be used as a therapeutic in the treatment of drug addiction, or ameliorating the craving for an addictive drug. The oligopeptide may be four to ten contiguous amino acids derived from the following portions of the mouse and human syndecan-3 sequence: RPGLGLHDNAIDSGSSAAQLLQKSILERKEVLVA (Seq. Id. No 1) or RPGPGLLDNAIDSGSSAAQLPQKSILERKEVLVA (Seq. Id. No 2). Thus, the oligopeptide may have the following sequences: RPGLGLHDNA (Seq. Id. No 3); RPGPGLLDNA(Seq. Id. No 4); LHDNAIDSGS (Seq. Id. No 5); LLDNAIDSGS (Seq. Id. No 6); IDSGSSAAQL (Seq. Id. No 7); SAAQLLQKSI (Seq. Id. No 8); SAAQLPQKSI (Seq. Id. No 9); LLQKSILERKE (Seq. Id. No 10); LPQKSILERKE (Seq. Id. No 11); and ILERKEVLVA (Seq. Id. No 12). A derivative of these oligopeptides may be resistant to peptidase cleavage. These include, for example, oligopeptides in which the N, C, or both the N and C termini, are protected from peptidase cleavage by an amide or ester group. Oligopeptides could also be modified, e.g. by conjugation to TAT, to facilitate crossing the blood brain barrier. Alternatively, to facilitate passage through the blood brain barrier and increase the amount of active oligopeptides in the brain, a lipophilic prodrug of the oligopeptide having an extended half-life could be formed. Lipophilic prodrugs could be formed by modifying the carboxylate groups on the oligopeptides to esters and modifying the amine groups to simple amides. Lipophilic prodrugs could also be formed by converting the acids and amines to other known shielding groups. Oligopeptides of the invention could be synthesized using conventional chemical synthesis techniques such as the Merrifeld method.

In another related embodiment, the above oligopeptides may be used for screening compounds that either inhibit the cleavage of syndecan-3 and/or promote the production or presence of syndecan-1 or a biologically active fragment thereof. In a particularly preferred embodiment peptide Seq. Id No. 3, for example, can be used to test compounds that active or inhibit the cleavage of said syndecans.

Pharmaceutical Composition of the Invention

In another embodiment, the invention provides a pharmaceutical composition having an inhibitor of the invention and a pharmaceutically acceptable carrier suitable for the route of administration. An inhibitor or pharmaceutical composition of the invention may be administered in numerous ways. For example, it may be administered orally, rectally, topically, or by intramuscular, intraperitoneal subcutaneous or intravenous injection. Preferably, it is administered orally or by injection. Other routes include intrathecal administration directly into spinal fluid and direct introduction onto, in the vicinity of or within the target cells.

The amount to be administered to the mammal can be any amount appropriate to prevent or treat drug addiction or ameliorate the craving for an addictive drug. The amount to be administered can be an effective dose or an appropriate fraction thereof. Such amounts will depend on individual patient parameters including age, physical condition, size, weight, the severity of the addiction, and any concurrent treatment. For example, the effective dose range that is necessary to prevent drug addiction can be significantly lower than the effective dose range for ameliorating the craving for a drug or treating drug addiction. Factors that determine appropriate dosages are well known to those of ordinary skill in the art and can be addressed with routine experimentation. For example, determination of the physicochemical, toxicological and pharmacokinetic properties can be made using standard chemical and biological assays and through the use of mathematical modeling techniques known in the chemical, pharmacological and toxicological arts. The therapeutic utility and dosing regimen can be extrapolated from the results of such techniques and through the use of appropriate pharmacokinetic and/or pharmacodynamic models. Dosages for administration to a patient will as understood by one of skill in the art.

An inhibitor of the invention can be administered orally or by injection at a dose of from 0.1 to 30 mg per kg weight of the mammal, preferably 2 to 15 mg/kg weight of the mammal. The dose range for adult humans is generally from 8 to 2,400 mg/day and preferably 35 to 1,050 mg/day. As certain inhibitors of the invention are long acting, it may be advantageous to administer an initial dose of 70 to 2,400 mg the first day then a lower dose of 20 to 1,200 mg on subsequent days. If the salt of an inhibitor of the invention is administered, then the amount of salt administered is calculated in terms of the base.

An inhibitor of the invention can be administered neat or, preferably, as pharmaceutical compositions. Pharmaceutical compositions of the invention include an appropriate amount of the inhibitor of the invention in combination with an appropriate carrier as well as other useful ingredients.

An inhibitor of the invention include those describe above, and wherein applicable, acceptable salts thereof or derivatives thereof. Acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic acid. Also, pharmaceutically-acceptable salts can be prepared as alkaline metal or alkaline earth salts, such as sodium, potassium or calcium salts of the carboxylic acid group. In addition, derivatives, e.g. protease resistant oligopeptides, as well as analogs of the foregoing oligopeptides that act as functional equivalents also are intended to be embraced as equivalents and within the scope of the invention.

A pharmaceutical composition of an inhibitor of the invention suitable for oral administration can be in the form of (1) discrete units such as capsules, cachets, tablets or lozenges each containing a predetermined amount of the drug; (2) a powder or granules; (3) a bolus, electuary or paste; (4) a solution or a suspension in an aqueous liquid or a non-aqueous liquid; or (4) an oil-in-water liquid emulsion or a water-in-oil liquid emulsion. For oral administration, an inhibitor of the invention can also be prepared with an enteric coating to prevent degradation in acidic environments. Compositions suitable for topical administration in the mouth, for example buccally or sublingually, include lozenges. Compositions suitable for parenteral administration include aqueous and non-aqueous sterile suspensions or injection solutions. Compositions suitable for rectal administration may be presented as a suppository.

Thus, a pharmaceutical composition of an inhibitor of the invention can be formulated using a solid or liquid carrier. The solid or liquid carrier would be compatible with the other ingredients of the formulation and not deleterious to the recipient. If the pharmaceutical composition is in tablet form, then the inhibitor is mixed with a carrier having the necessary compression properties in suitable proportions and compacted in the shape and size desired. If the composition is in powder form, the carrier is a finely divided solid in admixture with the finely divided active ingredient. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. A solid carrier can include one or more substances that may act as flavoring agents, lubricants, solubilizers, suspending agents, fillers, glidants, compression aids, binders or tablet-disintegrating agents. A suitable carrier may also be an encapsulating material.

If the composition is a solution, suspension, emulsion, syrup, elixirs or pressurized compositions, then liquid carriers can be used. In this case, the syndecan drug is dissolved or suspended in a pharmaceutically acceptable liquid carrier. Suitable examples of liquid carriers for oral and parenteral administration include (1) water, (2) alcohols, e.g. monohydric alcohols and polyhydric alcohols such as glycols, and their derivatives, and (3) oils, e.g. fractionated coconut oil and arachis oil. For parenteral administration, the carrier can also be an oily ester such as ethyl oleate and isopropyl myristate. Liquid carriers for pressurized compositions include halogenated hydrocarbon or other pharmaceutically acceptable propellant. The liquid carrier can contain other suitable pharmaceutical additives such as solubilizers; emulsifiers; buffers; preservatives; sweeteners; flavoring agents; suspending agents; thickening agents; colors; viscosity regulators; stabilizers; osmo-regulators; cellulose derivatives such as sodium carboxymethyl cellulose; anti-oxidants; and bacteriostats. Other carriers include those used for formulating lozenges such as sucrose, acacia, tragacanth, gelatin and glycerin as well as those used in formulating suppositories such as cocoa butter or polyethylene glycol.

If the composition is to be administered intravenously or intraperitoneally by infusion or injection, solutions of the inhibitor of the invention can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The composition suitable for injection or infusion may include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium as described above. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the inhibitor of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the syndecan drug, plus any additional desired ingredient present in the previously sterile-filtered solutions.

A pharmaceutical composition of the invention can be in unit-dose or multi-dose form or in a form that allows for slow or controlled release of the syndecan drug. Each unit-dose may be in the form of a tablet, capsule or packaged composition such as, for example; a packeted powder, vial, ampoule, prefilled syringe or sachet containing liquids. The unit-dose form also can be the appropriate number of any such compositions in package form. Pharmaceutical compositions in multi-dose form can be in packaged in containers such as sealed ampoules and vials. In this case, the inhibitor can be stored in a freeze-dried (lyophilized) condition requiring only the addition of a sterile liquid carrier immediately prior to use. In addition, extemporaneous injection solutions and suspensions can be prepared from sterile powders, granules and tablets of the kind previously described.

In another embodiment, the invention provides an article of manufacture comprising packaging material and, contained within the packaging material, a sheddase inhibitor. A sheddase inhibitor may be a MMP inhibitor, an ADAMs inhibitor or an inhibitor of other protease involved in the cleavage of syndecan-3 ectodomain. The packaging material may have a label indicating that the sheddase inhibitor may be used for preventing or treating drug addiction, or ameliorating the craving for an addictive drug.

Screening Methods

In another embodiment, the oligopeptides of the invention can also be used to identify the protease responsible for syndecan-3 cleavage. In one embodiment, these peptides can be labeled synthesized to incorporate internally quenched fluorescent groups that can be detected fluorescently upon cleavage in solution or in single or multidimensional separations by gel or chromatographical means.

In another embodiment, the invention provides a method for identifying an agent effective for preventing or treating drug addiction or ameliorating the craving for an addictive drug comprising (a) administering a test compound to a test animal and (b) determining the level of syndecan-3 cleavage in the animal such that if the level of syndecan-3 cleavage is lowered relative to a control, then the test compound is an agent effective for preventing drug addiction. The level of syndecan-3 cleavage in the animal can be determined from the level of full-length syndecan-3 or the level of the ectodomain of syndecan-3 in the brain of the animal, e.g. in the hypothalamus. The control may be another animal of the same species.

In another embodiment, the invention provides a method for screening for an agent effective for preventing or treating drug addiction or ameliorating the craving for an addictive drug comprising (a) administering a test compound to a syndecan-3 knockout mouse; and (b) determining whether the test compound reduces self-administration of the addictive drug in the mouse or ameliorates indices of motivation for the drug, reinstatement of drug taking on the presentation of a drug-associated cue after a period of abstinence, stress, priming by non-contingent administration of the drug or other model of reinstatement of drug-seeking behavior.

Animal Model

In another embodiment, the invention provides an animal model for screening for compounds that will decrease the craving for an addictive drug in a human or to determining neurobiological mechanisms involved in drug abuse in order to identify novel therapeutic targets. The model comprises a syndecan-3 knockout and/or whole syndecan-1 or syndecan-1 ectodomain transgenic mouse or another proteoglycan wherein the mouse exhibits (a) an increase or decrease frequency of self-administration of the addictive drug, or (b) an increase or decrease in one or more indices of motivation for the drug. Indices of motivation for the drug are known to those skilled in the art and include, without limitation, drug reward, anxiety and stress associated with withdrawal and abstinence, craving for the drug, reinstatement of drug taking after a period of abstinence induced by presentation of a drug associated cue, stress, or priming by non-contingent administration of the drug, conditioned place preference, escalation of drug intake, shift in the cocaine dose-response curve. These are described in Ahmed & Koob, Science 282:298-300 (1998); Kelley et al. Alcohol Clin Exp Res 21:1661-1666 (1997); Koob et al. Neurosci Biobehav Rev 27:739-749 (2004); Kosten et al. J Pharmacol Exp Ther 269:137-144 (1994); Lorrain et al. Behav Brain Res 107:9-19 (2000); Martellotta et al. Psychopharmacology (Berl) 132:1-5 (1997); Piazza et al., Brain Res 514:22-26 (1990); Shaham & Stewart, Psychopharmacology 111:523-527 (1994); Swerdlow & Koob Psychopharmacology (Berl) 84:163-166 (1984); Valjent & Maldonado Psychopharmacology (Berl) 147:436-438 (2000); and Weiss F Curr Opin Pharmacol 5:9-19 (2005), all of which are incorporated in their entirety herein by reference.

Examples of methods used to determine whether the test compound increases or decreases the rewarding and reinforcing properties of the addictive drug include self-administration in fixed ratio or progressive ratio paradigms, reinstatement of drug taking after a period of abstinence induced by presentation of a drug associated cue, stress, food deprivation, priming by non-contingent administration of the drug, other model of reinstatement of drug-seeking behavior or any other indices of motivation for the drug, drug reward, and reinforcement, including, but not limited to, conditioned place preference and aversion and any other indices of the mechanism of action of a drug including receptor binding or inhibition of binding, induction of cellular signaling, and drug-discrimination.

Unless otherwise defined, all technical and scientific terms used herein have the same meaning as commonly understood by one of ordinary skill in the art to which this invention belongs. Amino acid designations may include full name, three-letter, or single-letter designations as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. The present specification provides selected definitions of certain terms, and these definitions are preferred relative to other definition in the event that there are discrepancies. In addition, the materials, methods, and examples are illustrative only and not intended to be limiting.

Other features and advantages of the invention will be apparent from the following description and from the claims. The invention will be further described in the following examples, which do not limit the scope of the invention described in the claims.

EXAMPLES

Example 1

Rat Model of Escalation of Cocaine Self-administration

Rat Preparation. Rat were implanted with intravenous (IV) catheters under a 1-3% isoflurane/oxygen mixture. Following surgical implantation and appropriate wound closure, the animals were allowed a minimum of two days to recover prior to the beginning of the self-administration. Catheters were flushed daily with 250 μL of a sterile antibiotic solution containing heparinized saline (30 U/mL) and Timentin (100 mg/mL, SmithKline Beecham Pharmaceuticals, Philadelphia, Pa). Cathether patency was checked on a regular basis (twice a week) using a Brevital IV infusion (50 μL, 5 mg/mL). Cocaine HCl (NIDA, USA) was dissolved in sterile saline and made available for self-administration at a dose of 0.6 mg/kg/infusion over 4 seconds (infusion volume 15 μL). rat were trained to lever press for cocaine under a fixed-ratio-1 (20-s timeout, which occurred during the infusion) schedule of reinforcement for six to eight 1-hour daily sessions (Pre-escalating phase). Pre-escalation or baseline phase exposure to cocaine was carried out before test subjects were provided access to cocaine self-administration on an increased basis, specifically to six hours per day to induce escalation of cocaine intake as shown in Ahmed & Koob, (1988) Science 282: 298-300. Training continued until stable cocaine intake was established and the rats demonstrated a clear discrimination between the active and the inactive levers. Stable cocaine intake was defined as ≦20% variation in cocaine intake for three consecutive sessions. Clear discrimination between active and inactive levers was established when 75% of total responses were directed to the active lever.

Cocaine self-administration apparatus (Rat). Rats were individually placed in self-administration chambers (15.9×14×12.7 cm; Med Associates, Georgia, Vt.) located inside standard sound-attenuating cubicles equipped with a quiet ventilation fan. Drug infusions were delivered by a Razel syringe pump activated for 4 seconds to deliver cocaine in a volume of 15 μL through a Tygon tube attached to the catheter on the animal's back via a liquid swivel (Instech Labs, Plymouth Meeting, Va., USA) and a commercially available cannula connector (Plastics One, Roanoke, Va., USA). Chambers displayed two levers. Presses on the active lever led to cocaine delivery and a concomitant presentation of a cocaine-associated cue light for 20 seconds. During the 20 seconds, presses on the active lever did not activate the pump. Presses on the other lever were recorded but no cocaine was delivered and no cue light was presented.

Example 2

Changes in Gene Expression in a Rat Model of Escalation of Cocaine Intake

A rat model of escalation of cocaine intake was used to identify changes in gene expression with increasing cocaine intake. In the model, rats were implanted with chronic silastic jugular catheter for cocaine self-administration as described above. Rats were then allowed access to cocaine for one hour each day (short access (ShA)) or for six hours each day (long access (LgA)) for eight days. Rats allowed LgA to cocaine self-administration exhibit escalated cocaine intake, while those allowed ShA to cocaine display a stable level of cocaine intake. The data, shown in FIG. 1A, represent the mean (±s.e.m.) number of cocaine injections obtained during the first hour of each daily self-administration session. The "*" indicates where LgA and ShA rats differ ($p<0.05$, tests of simple main effects after appropriate two-way analyses of variance).

Using high-density oligonucleotide arrays (Affymetrix, RNU34), gene expression profiles were determined for reward-related brain regions of rats that have been allowed LgA to cocaine self-administration. Rats that have been allowed ShA to cocaine self-administration as well as cocaine naive rats were used as controls. The brain regions examined included the prefrontal cortex, nucleus accumbens, septum, lateral hypothalamus, amygdala, and ventral tegmental area. Results were analyzed using four methods: (a) Affymetrix Microarray Suite 4 (MAS4); (b) Affymetrix Microarray Suite 5 (MASS); (c) dCHIP; and (d) RMA. The MAS4 and MASS methods used perfect match minus mismatch models, while dCHIP and RMA use perfect match only models to generate expression values. Results were also validated by RT-PCR in individual animals from an independent replication of the experiment. FIG. 1B summarizes the number of genes in different brain regions of LgA rats that changed by more than 1.4 when brain regions of LgA rats were compared to that of (1) drug-naive control rats (CSA genes, white bars) or (2) ShA and drug-naive rats (ESC genes, black bars). In FIG. 1B, VTA refers to ventral tegmental area; LH refers to the lateral hypothalamic area; AMG refers to amygaloid complex; NAc refers to nucleus accumbens; SEP refers to the septal area; and MPF refers to medial prefrontal cortex.

Thus, a small number of genes was found to'e associated with escalated cocaine intake (ESC genes). Unexpectedly, of the brain regions examined, the lateral hypothalamus (LH) was the most transcriptionally responsive in escalation of cocaine intake (FIG. 1B). Most of the ESC genes identified were also expressed during synaptogenesis and synaptic plasticity. These include genes that code for several pre- and post-synaptic proteins involved in neurotransmission (Ahmed et al., (2005) *Proc. Natl. Acad. Sci. USA* 102:11533-8). These results suggest that LH intrinsic circuitry undergoes a structural reorganization during escalation of cocaine use, which could contribute to the chronic deficit in reward function that has been hypothesized to drive the transition to compulsive drug taking and addiction (Ahmed et al., (2002) *Nat. Neurosci.* 5:625-626).

Figure 2:
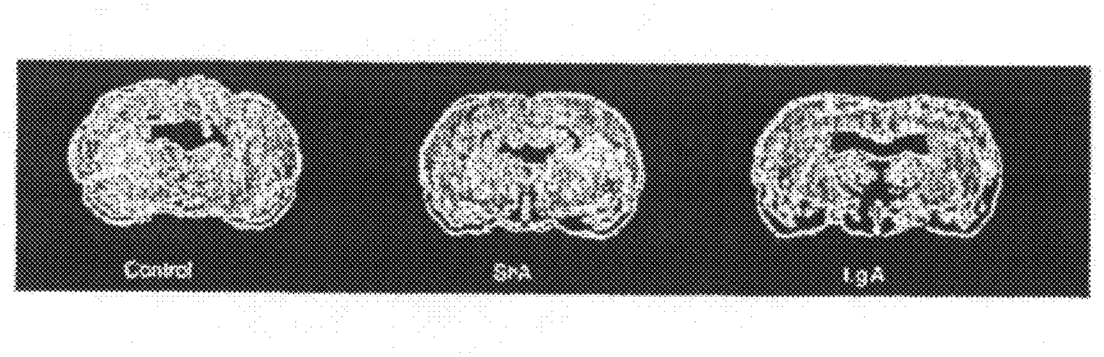
FIG. 2 illustrates the induction of syndecan-3 mRNA expression in the hypothalami of a rats given short term access and long term access to cocaine self-administration as determined by in situ hybridization in comparison to a control rat. Signal intensity is indicated as follows: blue<green<yellow<red.

Syndecan-3, a gene previously associated with feeding behavior, demonstrated the highest increase when rats allowed LgA were compared to control rtas. In situ hybridization demonstrated a diffuse increase of expression of syndecan-3 mRNA in the hypothalami of rats allowed ShA and LgA to cocaine self-administration (FIG. 2) when compared to control rats (*$p<0.01$ by ANOVA with Fischer PLSD post hoc test). Replication of the hybridizations reported by Ahmed et al. (Ahmed et al., 2005) with a more comprehensive array (RAE230A) showed that the mRNA levels of tissue inhibitor of metalloprotease-3 (TIMP-3) were also increased in the hypothalami of LgA rats. TIMP-3 inhibits a yet unidentified sheddase that acts to terminate the action of Syndecan-3. See Reizes et al., (2003) *Ann. N.Y. Acad. Sci.* 994:66-73. The normalized, MAS-5-derived expression values for TIMP-3 were: (a) 1.028 (+0.028) for control rats; (b) 0.802 (+0.053) for rats allowed ShA to cocaine; and (c) 1.555

(+0.075) for rats allowed LgA to cocaine. Syndecan-3 mRNA was significantly increased in ShA and LgA rats over controls.

Together these data suggest that a history of cocaine self-administration activates hypothalamic syndecan activity by inducing transcription of syndecan-3 as well as transcription of TIMP-3, the endogenous inhibitor of syndecan-3 processing. The role of syndecan-3 in cocaine self-administration was then investigated with mutant mice.

Example 3

Cocaine Self-administration Patterns in Syndecan-3 Knockout Mice, Whole Syndecan-1 Transgenic Mice and Syndecan-1 Ectodomain Transgenic Mice Four mouse genotypes were used in the following experiments. Syndecan-3 knockout mice, whole syndecan-1 transgenic Mice and syndecan-1 ectodomain transgenic mice are as described in Reizes et al. (2001) *Cell* 106:105-116 and wildtype mice. Since syndecan-1 is not cleaved in the brain, whole (full-length) syndecan-1 transgenic mice represent mice having a constitutive active allele of syndecan. Conversely, transgenic mice expressing the ectodomain of syndecan-1, that is, the product of cleavage of syndecan-1 mimic the expression of a constitutively shed syndecan. The latter group of mice demonstrated that the protective effects is due to uncleaved or at least a more complete segment of syndecan-1, which mimics the action of full-length syndecan-3 because of its resistance to proteinase cleavage in the brain (Reizes et al., 2001 *Cell* 106:105-116). Syndecan-3 is mostly cleaved in the brain (Hsueh & Sheng (1999) *Neurosci.* 19:7415-25). Syndecan-3 knockout mice and syndecan-1 transgenic mice were previously backcrossed to C57BL/6J for more than eight generations (Strader et al. (2004) *J. Clin. Invest.* 114:1354-1360). As shown by Strader et al., syndecan mutants in C57BL/6J background kept on a low-fat diet did not substantially differ in body weight.

Syndecan-3 knockout mice and syndecan-1 transgenic mice were implanted with chronic silastic jugular catheters for cocaine self-administration as described above. Mice so prepared were allowed to self-administer cocaine under the following schedule: 7 days of 1-hour access to self-administration (short access, ShA or baseline) followed by 8 days of 6-hour access (long access, LgA or escalation).

Figure 3:
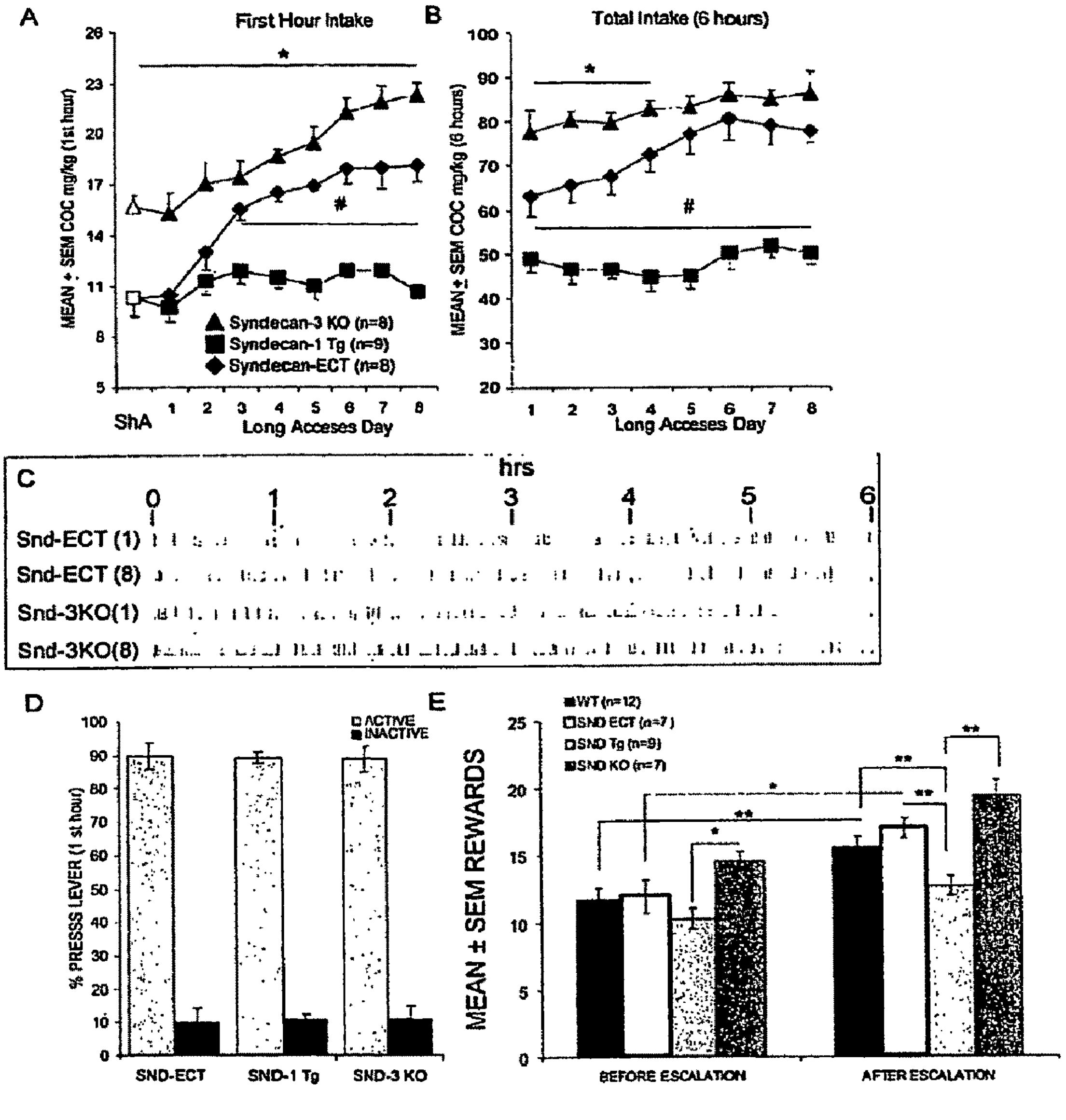
FIGS. 3A-E show comparisons of cocaine self-administration patterns of Syndecan-3 knockout mice, Syndecan-1 transgenic mice and wild type mice. The graph in FIG. 3A is a graph comparing the cocaine intake in the first hour by syndecan-3 knockout mice, whole (full-length) syndecan-1 transgenic mice and mice expressing synecan-1 ectodomain allowed long (6 hrs) access to cocaine over eight days (a model of loss of control over intake).

During the ShA phase of the experiment, cocaine intake did not differ between mice expressing syndecan-1 ectodomain transgenic (syndecan-ECT) and whole syndecan-1 transgenic (syndecan-1 Tg) mice. This is shown in FIG. 3A, white symbols at "ShA" (white square corresponds to cocaine intake of syndecan-1 Tg and white diamond corresponds to cocaine intake of syndecan-ECT on the last day of the ShA phase). In contrast, cocaine intake by syndecan-3 knockout (KO) mice was significantly higher than cocaine intake by the wild-type control and syndecan-1 transgenic mice ($p<0.01$) during the ShA phrase of the experiment. This is shown in FIG. 3A, white triangle at "ShA" (value corresponds to cocaine intake by syndecan-3 KO mice on the last day of the ShA phase).

During the LgA phrase of the experiment, cocaine intake in the first hour by syndecan-3 knockout and wild-type mice showed significant escalation over the 8 days. This is shown in FIG. 3A, black triangle (syndecan-3 KO mice) and black diamond (syndecan-ECT]). In contrast, cocaine intake by whole syndecan-1 Tg mice in the first hour of the 6-hour access period did not escalate over the 8 days as shown in FIG. 3A (black squares). Interestingly, while cocaine intake by syndecan-3 KO mice over the first hour was significantly higher than that by syndecan-ECT transgenic mice throughout the LgA phase of the experiment (FIG. 3A), by the $4^{th}$ LgA day, total intake over the 6 hours of daily access was not significantly different between the two strains (FIG. 3B). This reflected a progressively earlier loading of cocaine intake in syndecan-3 KO mice—reminiscent of the binge pattern of intake in humans—and, possibly, a ceiling effect due to cocaine-induced somatic effects (FIG. 3C). (for FIGS. 3A, 3B: *$P<0.05$/$P<0.01$ by ANOVA with Fischer PLSD post hoc test). Lever pressing was highly selective as about 90% of the responses of all three mice genotypes were on the active lever, thereby ruling out the possibility of a motor effect of cocaine at this dose on the performance of the mice (FIG. 3D).

Progressive ratio (PR) tests, a measure of the 'motivational' state of the animal, were performed before and after escalation of cocaine intake. PR formula was (5×exp(reinforcer number×0.2)−5) which yields values of 1, 2, 4, 6, 9, 12, 15, 20, 25, 32, 62, 77, 95, 118, 145, 178, 219, 268, et cetera.

Rewards earned with the PR schedule of reinforcement is considered to be an indicator of the amount of effort an animal is willing to expend to obtain a reward, in this case, cocaine injections. No significant difference was seen between the mean number of rewards earned by syndecan-1 Tg, syndecan-ECT and wildtype (WT) mice before escalation. Although Syndecan-3 KO mice did not earn significantly more rewards than syndecan-1 Tg transgenic mice, they did earn significantly more rewards than syndecan-ECT and WT mice (*$P<0.05$ by ANOVA with Fischer PLSD post hoc test) as indicated in FIG. 3E. After escalation, WT and syndecan-ECT mice earned significantly more rewards (**$p<0.01$; *$p<0.05$, respectively) than they did before escalation. In contrast, both whole syndecan-1 Tg mice and syndecan-3 KO did not earn significantly more rewards after escalation than before escalation (FIG. 3E). After escalation, WT, syndecan-3 KO and syndecan-ECT mice earned more rewards than whole (full-length) syndecan-1 transgenic mice (**$p<0.01$). Thus expression of full-length syndecan-1 in transgenic mice prevented the increased motivation to take cocaine that is associated with escalated (i.e. dependent) cocaine intake.

Cocaine self-administration apparatus (Mouse). Mouse were individually placed in self-administration chambers (5$\frac{9}{16}$×5½×6½ inch) located inside standard sound-attenuating cubicles equipped with a quiet ventilation fan. Drug infusions were delivered by a Razel syringe pump activated for 4 seconds to deliver cocaine in a volume of 15 μL through a Tygon tube attached to the catheter on the animal's back via a liquid swivel (Instech Labs, Plymouth Meeting, Va., USA) and a commercially available cannula connector (Plastics One, Roanoke, Va., USA). Chambers displayed two levers. Presses on the active lever led to cocaine delivery and a concomitant presentation of a cocaine-associated cue light for 20 seconds. During the 20 seconds, presses on the active lever did not activate the pump. Presses on the other lever were recorded but no cocaine was delivered and no cue light was presented.

Example 4

Effect of Syndecan Expression on Cue-induced Reinstatement of Cocaine-seeking-behavior in Mice Training phase. Mice were prepared with chronic silastic jugular catheters for cocaine self-administration as described above. Separate groups of mice of the 3 syndecan mutant genotypes (syndecan-3 knockout, whole syndecan-1 transgenic, and syndecan-1 ectodomain transgenic mice) were trained to self-administer cocaine by intravenous injection as described above. Mice were subjected to 7 sessions of 1-hour access to self-administration followed by 8 sessions of 6-hour access as described above. During this phrase, presses on the active lever led to cocaine infusion, and this was accompanied by presentation of cue light.

Extinction phase. During the extinction phrase, presses on the lever previously associated with cocaine delivery did not lead to cocaine administration or presentation a cue-light that had been paired with cocaine infusions during the training phrase. Mice were allowed one 1-hour extinction session/day for a minimum of 14 days, until an extinction criterion was reached. The extinction criterion was designated as a group mean of less than 10 responses/1 hour for two consecutive sessions on the active lever.

Test for reinstatement. The conditions during testing were identical to those during the extinction phase, with the exception that lever presses led to presentations of the cocaine cue-light for 5 seconds. The 1-hour test session for cue-induced reinstatement were conducted on the day following the last extinction session. A one way ANOVA with one between factor (genotype, three) were used to measure any differential effects of the cocaine-related cue induced reinstatement.

Figure 4:
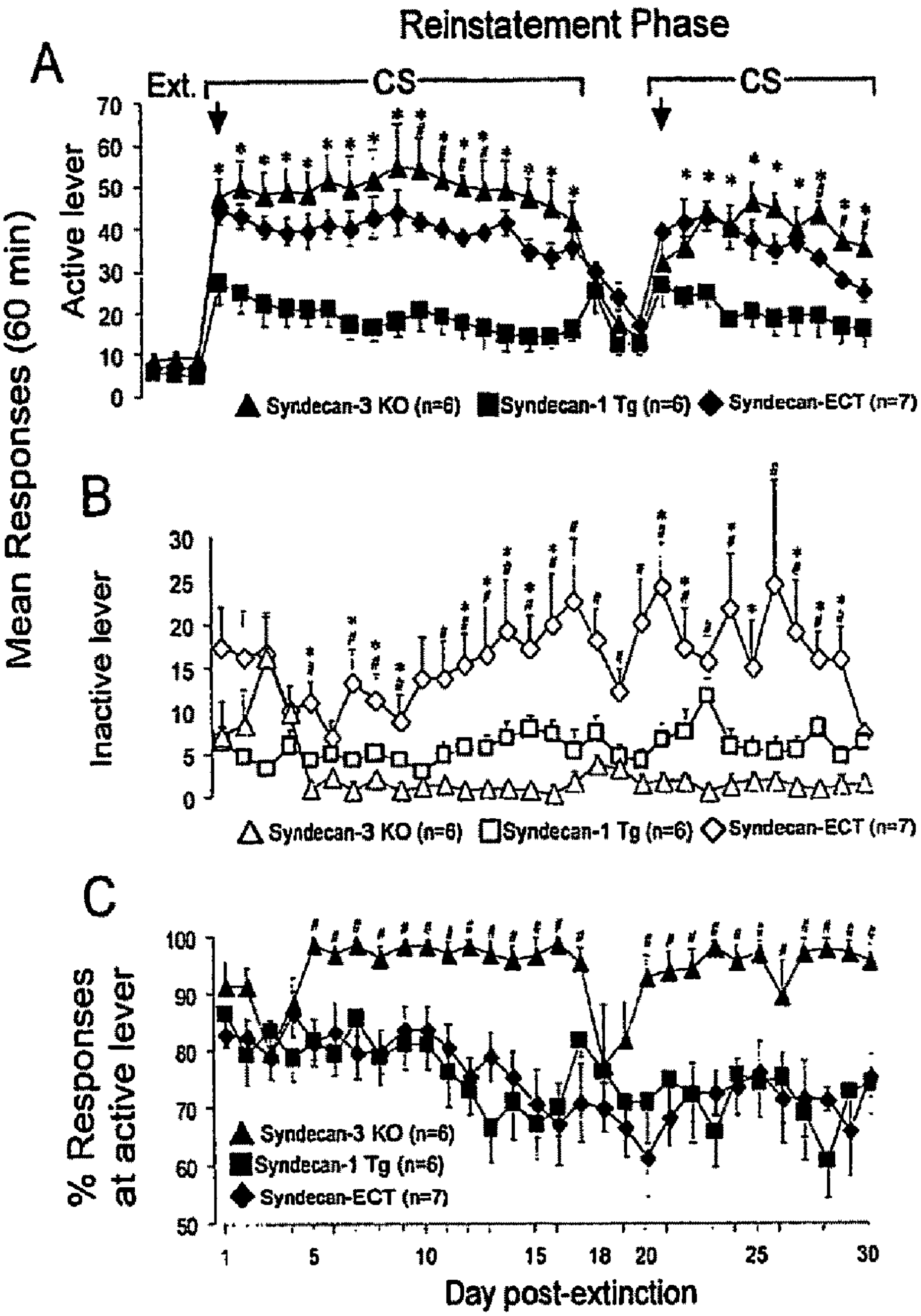
FIGS. 4A-C are graphs showing that expression of whole (full length) syndecan-1 reduces reinstatement of cocaine-seeking behavior in mice.

Results. FIG. 4A shows the active lever press responses during the last three one-hour sessions of extinction (Ext.) and cue-induced reinstatement (Reinstatement Phrase). At the beginning of the first reinstatement session (black arrows), the cue light was presented non-contingently once for 5 seconds, after which time lever presses were associated with the 20-second cue light. Horizontal bracket labeled CS indicates contingent presentation of the cue light during reinstatement. Syndecan-3 knockout mice (syndecan KO, black triangles, n=6) and syndecan-1 ectodomain transgenic mice (syndecan-ECT, black diamonds, n=7) responded significantly more than whole syndecan-1 transgenic mice (syndecan-1 Tg, black squares, n=6) (see FIG. 4A). In addition, syndecan-3 knockout mice appeared slightly more resistant to extinction of cue-induced cocaine-seeking behavior (*indicates that the behavior of syndeacan-3 knockout mice and syndecan-1 ectodomain transgenic mice was significantly different from whole syndecan-1 transgenic mice, $p<0.05/p<0.01$; # indicates that the behavior of syndeacan-3 knockout mice was significantly different from wild-type mice, $p<0.05/p<0.01$).

FIG. 4B shows the inactive lever press responses of the three mice genotypes. Syndecan-3 knockout mice (white triangles) responded significantly less than both syndecan-1 ectodomain (white diamonds) transgenic mice and whole syndecan-1 transgenic mice (white squares) on the inactive lever.

FIG. 4C shows the % responses at the active lever for the three mice genotypes. Syndecan-3 knockout mice (black triangles) had a percentage response near 100% at the active lever when the cue light was present (CS). This was significantly higher (#$p<0.05/p<0.01$) than syndecan-1 ectodomain (black diamonds) transgenic mice or whole syndecan-1 transgenic mice (black squares). In contrast, the % responses at the active lever demonstrated by syndecan-1 ectodomain transgenic mice or whole syndecan-1 transgenic mice did not show a significant difference. This suggests that a lack of syndecan-3 is associated with a narrowing of the behavioral repertoire to cocaine-seeking behavior, a criterion of addiction.

Note that during sessions 18-20 the cue light was withdrawn, resulting in an abatement of response in all groups and a dramatic decrease in the percent responding at the active lever in the syndecan-3 knockout mice. At session 21 the cue light was again presented non-contingently once for 5 seconds (black arrow). After session 21, lever pressing again led to presentation of the cue light. This resulted in increased response. *Significantly different from syndecan-1 transgenic mice (both for syndecan-3 KO mice and syndecan-1 ectodomain transgenic mice), $p\leqq 0.05/p\leqq 0.01$. #Significantly different between syndecan-3 knockout mice and syndecan-1 ectodomain transgenic mice, $p\leqq 0.05/p\leqq 0.01$.

Example 5

Cocaine Intake by Mice Administered GM-6001

Figure 5:
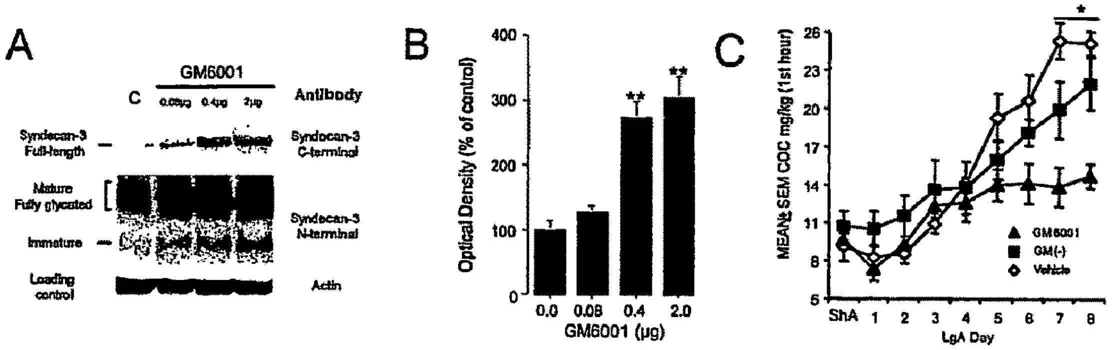
FIGS. 5A, B, and C are graphs showing that the wide-spectrum proteinase inhibitor GM6001 (ilomastat) prevented escalation of cocaine intake (a model of loss of control over intake) in animals allowed long (6 hrs) access to cocaine.
FIG. 5B is a bar graph showing a quantification of the western blot using a syndecan-3 C-terminal domain-specific antibody shown in FIG. 5A.
FIG. 5C is a graph comparing the amounts of cocaine intake in the first hour of the escalation phase by (a) mice that were given the wide-spectrum metalloproteinase inhibitor GM-6001 (0.4 μg/mouse) before the self-administration session and (b) by mice that were given the vehicle alone.

FIG. 5A. Normal C57BL/6J mice were administered the wide-spectrum metalloproteinase inhibitor GM-6001 intracerebroventricularly (ICV) at various doses and were were sacrificed 3 hours after administration. GM-6001 resulted in the accumulation of uncleaved syndecan-3 as demonstrated by western blotting with an antibody to the syndecan-3 C-terminal intracellular domain.

FIG. 5B. Quantification of western blot shown in (A). Uncleaved syndecan-3 was increased by about 3 fold at the highest doses tested ( $p<0.01$ from vehicle-injected control; the increase seen at 0.4 μg was not significantly different from that at 2.0 μg, therefore the latter dose was used for testing in the cocaine escalation paradigm in 5**C.

FIG. 5C. Normal C57BL/6J mice were allowed to self-administer cocaine for 1 hour per day for 7 days (short access, ShA). These mice were then assigned to two groups and each group was allowed to self-administer cocaine for 6 hours per day (long access, LgA) in order to induce an escalated pattern of cocaine intake. During the escalation phase, one group received an intracerebroventricular (ICV) injection of the wide-spectrum metalloproteinase inhibitor GM-6001 (0.4 μg/mouse) before the self-administration session (red triangles, n=11), while the other group reveived the structurally related, but inactive compound n-t-butoxycarbonyl-L-leucyl-L-tryptophan methylamide [GM(−), black squares, n=5); and a third group received the vehicle alone (yellow diamonds, n=5). Amounts of cocaine self-administered by the two groups of mice, given as mg cocaine/kg mean body weight. Amounts of cocaine intake over the first hour of the 6 hours of self-administration is shown. ShA indicates the number of cocaine injections on day 7 of the short access phase. Results showed that mice that received either the vehicle or the inactive control compound readily escalated their cocaine intake. Mice that received the wide-spectrum metalloproteinase inhibitor did not exhibit the same pattern of escalated cocaine intake. The number of cocaine injections self-administered by control mice was significantly greater than that by mice given the inhibitor as indicated by the results of day 7 and 8 (*$p<0.05/p<0.01$).

Example 6

Figure 6:
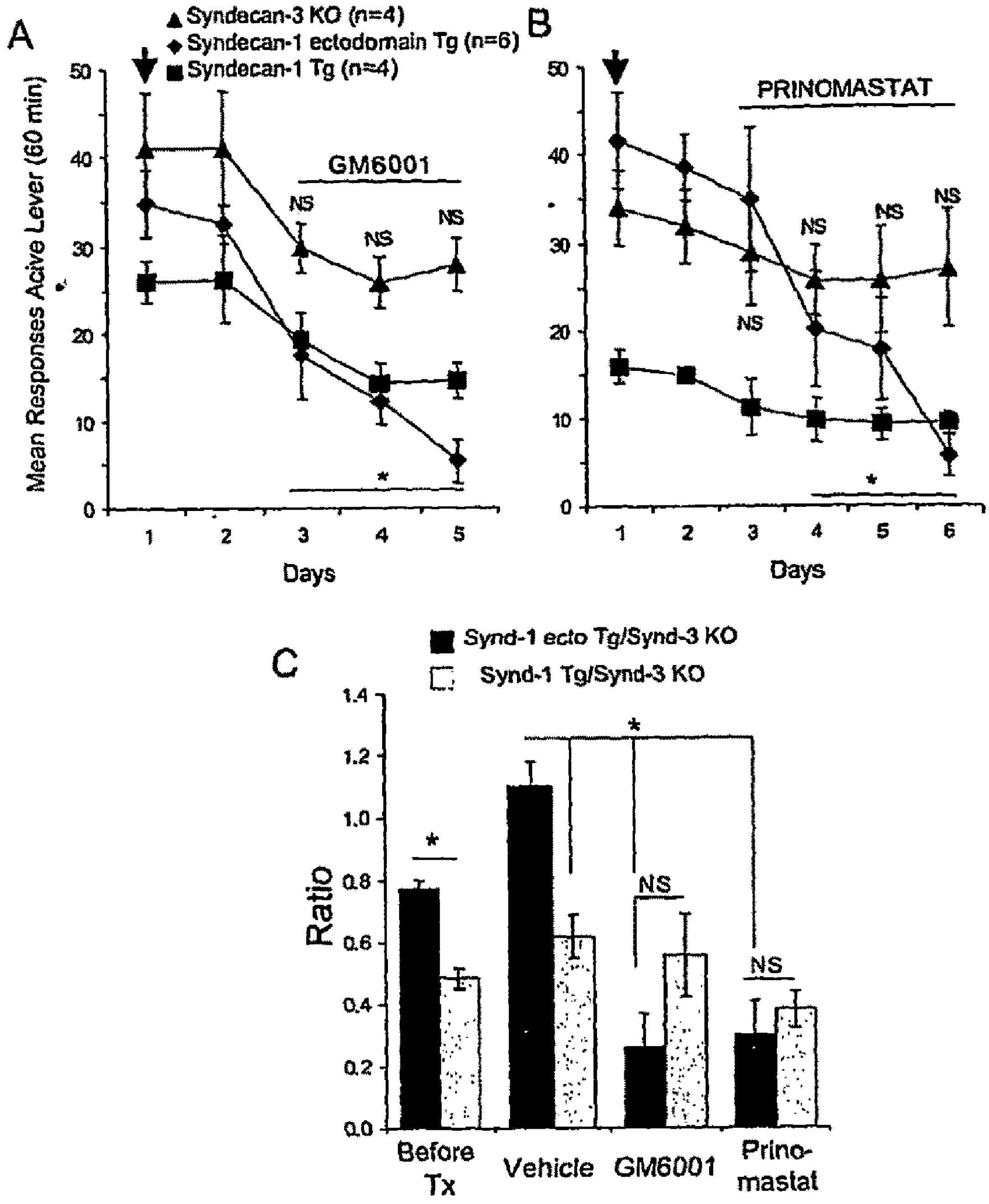
FIGS. 6A, B, and C are graphs showing that both GM6001 and prinomastat block reinstatement of cocaine seeking behavior in mice.
FIG. 6B is a graph that shown inhibition of cocaine-seeking behavior by prinomastat.
FIG. 6C is a graph that shows that MMP inhibitors were effective in significanity reducing cocaine-seeking behavior in syndecan-1 ectodomain transgenic mice but not in syndecan-3 knockout mice.

Wide-Spectrum MMP Inhibitors Block Cue-Induced Reinstatement of Cocaine-Seeking Behavior In still another example, the following experiment was performed showing that a wide spectrum of MMP inhibitors block cue-induced reinstatement of cocaine seeking behavior. Lever-pressing behavior in cocaine self-administering syndecan-mutant mice was extinguished in the absence of the 20 sec cue light (CS) that was paired with cocaine infusions during the training phase as shown in Example 4. In FIG. 6A, Syndecan-3 KO mice (black triangles) and syndecan-1 ectodomain Tg mice (black diamonds) responded significantly more than whole (full-length) syndecan-1 Tg mice (black squares) were presented with the cue light non-contingently once for 5 sec to reinitiate cocaine-seeking behavior. ICV injection of GM6001 (0.4 μg) 30-60 min before the reinstatement sessions starting on the third session greatly reduced cocaine seeking behavior in whole syndecan-1 Tg mice (*$p<0.01$ from the last day before initiation of treatment). Conversely responding in syndecan-3 KO mice was not significantly different from the last day before treatment and the last day of treatment (NS). In FIG. 6B, After a few days, animals were again presented with the cue light non-contingently and on the third day of reinstatement they were administered IP the systemically active broad-spectrum MMP inhibitor prinomastat (20 mg/Kg) 30-60 min before the reinstatement sessions starting on the third session. Prinomastat that readily crosses the blood-brain barrier was administered intraperitoneally (IP) at 20 mg/Kg. Again responding significantly declined in syndecan-1 ectodomain Tg mice (* $p<0.01$ from the last day before initiation of treatment) but not in syndecan-3 KO (NS). Prinomastat did not affect performance on the rotarod at the dose used suggesting that systemic administration of prinomastat does not impact general motor activity (not shown). FIG. 6C shows that the ratio of the responses of syndecan-1 ectodomain Tg mice to those of syndecan-3 KO mice before treatment and in vehicle-treated mice was significantly higher than the ratio of whole syndecan-1 Tg to syndecan-3 KO, consistent with the greater level of responsing of syndecan-1 ectodomain Tg and syndecan-3 KO mice. Treatment with either MMP inhibitor significantly decreased the response ratio of syndecan-1 ectodomain Tg to syndecan-3 KO mice which, on the last day of treatment was not significantly different from the response ratio of whole syndecan-1 Tg to syndecan-3 KO (* $p<0.01$, NS: non-significant). n=4-6.

Example 7

Figure 7:
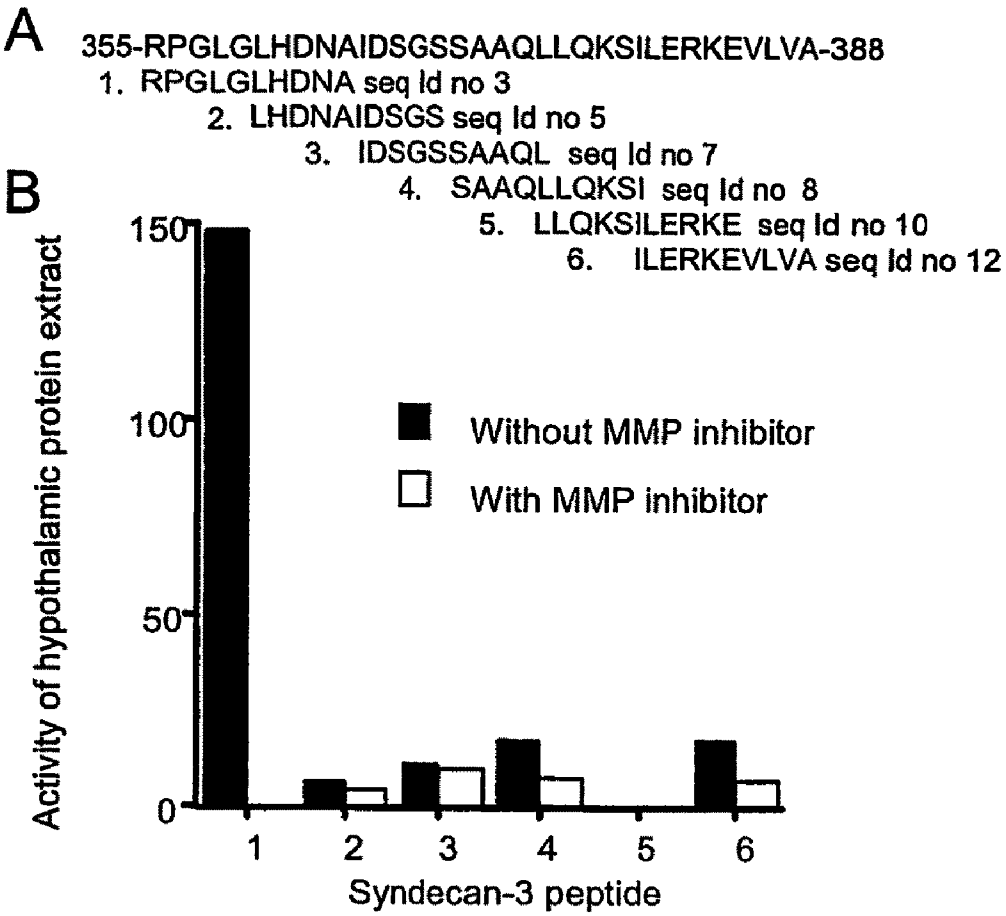
FIGS. 7A and B are a set of overlapping polypeptides and a graph showing specific cleavage of peptides derived from syndecan-3 following incubation with hypothalamic protein extracts.
FIG. 7B shows a Graph shows peptide 1 (Seq. Id. No 3 was cleaved by hypothalamic protein extracts while the other peptides were not.

Identification of Syndecan-3 Site of Shedding and Establishment of an Assay for the Identification of the Syndecan-3 Sheddase in the Hypothalamus According to one of the embodiments of the invention, syndecan-3 sheddases are identified by an assay for syndecan-3 cleavage, which requires knowledge of the cleavage site. The cleavage site for syndecan-3 cleavage is not presently completely identified. However, according to embodiments of the invention, we designed a battery of overlapping internally-quenched fluorogenic peptides spanning the juxtamembrane region of the mouse syndecan-3 (Amino Acid residues 355-388) labeled at their ends with Abz (ortho-aminobenzoyl) and EDDnp (ethylenediaminedinitrophenyl) for fluorescent detection of proteolytic cleavage (FIG. 7A). The peptides were individually incubated with mouse hypothalamic protein extracts at 37° C. in 50 mM Tris-HCl buffer, pH 7.0. Fluorescence was continuously measured at $\lambda_{ex}$=320 nm and $\lambda_{em}$=420 nm. Peptide 1 (Seq Id. No. 3) was efficiently hydrolized in and manner sensitive to the MMP inhibitor ortho-phenanthroline consistent with proteolysis by a metalloprotease. This experiment established this peptide as a substrate for the syndecan-3 sheddase and indicates that the site of cleavage is likely to be RPGLG. Proteolytic activity is expressed as reaction rate (activity/μl/min). When incubated with hypothalamic extract, strong proteolytic activity was seen on one of such peptides, peptide 1 (P1), (Seq Id No. 3), indicating that syndecan-3 cleavage site in the hypothalamus is within this peptide and likely at the G-L bond (355-RPGLG/LHDNAQ-364) as glycine in P1 is common in metalloproteases substrates (FIG. 7B). The reaction was completely inhibited by the MMP inhibitor ortho-phenanthroline, supporting that, as expected, the enzyme responsible for the cleavage is a metalloprotease. Thus, this peptide or a peptide overlapping this peptide can be used in an assay to identify the sheddase of syndecan-3 and/or drugs that prevent or facilitate shedding (inhibitors, activators, mimics antimimics).

We have also observed activity of hypothalamic extracts on a fluorogenic substrate peptide cleaved by the tumor necrosis factorα converting enzyme (TACE or ADAM17) and related proteases such as ADAM9 and 10 (peptide E003, Mca-PLAQAV-Dpa-RSSSR-NH2 (Seq. Id. No 13), R&D Biosystems, Minneapolis, Minn.), this result indicates this group of related ADAMs are primary candidates for syndecan-3 shedding in the mouse hypothalamus. Interestingly, while several MMPs were found to be expressed at low levels in the hypothalamus, MMP9 that is responsible for cleavage of syndecan-1 in other systems [Brule, s. et al. (2006) Glycobiology 16:488-501], was clearly absent in apparent agreement with the lack of cleavage of transgenic syndecan-1 in the hypothalamus. While the invention has been described in conjunction with the detailed description, the foregoing description is intended to illustrate and not limit the scope of the invention, which is defined by the scope of the appended claims. Other aspects, advantages, and modifications are within the scope of the following claims.

What is claimed is:

1. An animal model system for screening compound(s) for use in decreasing craving for an addictive drug in a mammal comprising:

(a) Providing a syndecan-3 knockout mouse;

(b) Providing a mouse of the same species as said syndecan-3 knockout mouse that is not itself a syndecan-3 knockout mouse and is transgenic for whole (full-length) syndecan-1 or syndecan-1 ectodomain, and;

(c) Allowing said mice of (a) and (b) to self-administer an addictive drug;

(d) Administering to said mice (a) and (b) a compound; and (e) Observing a decrease in the frequency of self-administration or decrease in at least one indices of motivation for the drug in said mouse of (a) relative to mouse of (b), following administration of said compound, Wherein compounds associated with a decrease in self-administration or a decrease in one or more indices of motivation, or craving for an addictive drug are identified.

2. The animal model of claim 1 wherein said mouse of (a) exhibits either an increased frequency of self administration of the addictive drug, or an increase in one or more indices of motivation for the drug, relative to a mouse of (b).

3. The animal model of claim 2 wherein said mouse of (a) exhibits an increased frequency of self administration of an addictive drug cocaine relative to the frequency of self-administration of said drug by a mouse of (b).

4. The animal model of claim 2 wherein said mouse of (a) exhibits a decreased frequency of self administration of the addictive drug relative to the frequency of mouse of (b) following administration to said mice of (a) and (b) a matrix metalloprotease inhibitor (MMP) or an inhibitor of syndecan-3 ectodomain cleavage thereby identifying a compound that decreases craving for the addictive drug.

5. The animal model of claim 4 wherein the compound is selected from the group consisting of metalloprotease inhibitor GM-6001, prinomastat, an agent that inhibits N-acetylgalactosaminyltransferase such as a nucleosidyl shift base, an inhibitor of disintegrin and metalloprotease (ADAM).

6. The animal model of claim 5 wherein said indices of motivation for the drug are selected from the group consisting of anxiety and stress associated with withdrawal and abstinence, craving for the drug, reinstatement of drug taking after a period of abstinence induced by presentation of a drug associated cue, and stress.

7. An animal model for screening compounds for use in decreasing craving for an addictive drug in a human comprising:

(a) Providing a syndecan-3 knockout mouse, wherein said mouse exhibits either an increased frequency of self administration of the addictive drug, or an increase in one or more indices of motivation for the drug, relative to a mouse of the same species that is transgenic for whole (full-length) syndecan-1 or syndecan-1 ectodomain;

(b) Providing a mouse of the same species as said syndecan-3 knockout mouse of (a), that is transgenic for whole (full-length) syndecan-1 or syndecan-1 ectodomain;

(c) Allowing to said mice of (a) and (b) to self-administer an addictive drug, wherein said mouse of (a) exhibits either an increased frequency of self administration of the addictive drug, or an increase in one or more indices of motivation for the drug, relative to a mouse of (b);

(d) Administering to said mice (a) and (b) said compound; and (e) Observing a decrease in the frequency of motivation in said mouse of (a) relative to mouse of (b), or Measuring one or more indices of motivation following the administration of said compound wherein mouse of (a) shows a decrease in motivation for the drug;

Wherein compounds associated with a decrease in self-administration or a decrease in one or more indices of motivation, or craving for an addictive drug are identified.

* * * * *

SEQUENCE LISTING

```
<160> NUMBER OF SEQ ID NOS: 13

<210> SEQ ID NO 1
<211> LENGTH: 34
<212> TYPE: PRT
<213> ORGANISM: Mus musculus

<400> SEQUENCE: 1

Arg Pro Gly Leu Gly Leu His Asp Asn Ala Ile Asp Ser Gly Ser Ser
 1              5                   10                  15

Ala Ala Gln Leu Leu Gln Lys Ser Ile Leu Glu Arg Lys Glu Val Leu
            20                  25                  30

Val Ala
```

<210> SEQ ID NO 2
<211> LENGTH: 34
<212> TYPE: PRT
<213> ORGANISM: Homo sapiens

<400> SEQUENCE: 2

```
Arg Pro Gly Pro Gly Leu Leu Asp Asn Ala Ile Asp Ser Gly Ser Ser
 1               5                  10                  15

Ala Ala Gln Leu Pro Gln Lys Ser Ile Leu Glu Arg Lys Glu Val Leu
            20                  25                  30

Val Ala
```

<210> SEQ ID NO 3
<211> LENGTH: 10
<212> TYPE: PRT
<213> ORGANISM: Mus musculus

<400> SEQUENCE: 3

```
Arg Pro Gly Leu Gly Leu His Asp Asn Ala
 1               5                  10
```

<210> SEQ ID NO 4
<211> LENGTH: 10
<212> TYPE: PRT
<213> ORGANISM: Homo sapiens

<400> SEQUENCE: 4

```
Arg Pro Gly Pro Gly Leu Leu Asp Asn Ala
 1               5                  10
```

<210> SEQ ID NO 5
<211> LENGTH: 10
<212> TYPE: PRT
<213> ORGANISM: Mus musculus

<400> SEQUENCE: 5

```
Leu His Asp Asn Ala Ile Asp Ser Gly Ser
 1               5                  10
```

<210> SEQ ID NO 6
<211> LENGTH: 10
<212> TYPE: PRT
<213> ORGANISM: Homo sapiens

<400> SEQUENCE: 6

```
Leu Leu Asp Asn Ala Ile Asp Ser Gly Ser
 1               5                  10
```

<210> SEQ ID NO 7
<211> LENGTH: 10
<212> TYPE: PRT
<213> ORGANISM: Mus musculus

<400> SEQUENCE: 7

```
Ile Asp Ser Gly Ser Ser Ala Ala Gln Leu
 1               5                  10
```

<210> SEQ ID NO 8
<211> LENGTH: 10
<212> TYPE: PRT
<213> ORGANISM: Mus musculus

<400> SEQUENCE: 8

```
Ser Ala Ala Gln Leu Leu Gln Lys Ser Ile
```

-continued

```
 1               5                   10


<210> SEQ ID NO 9
<211> LENGTH: 10
<212> TYPE: PRT
<213> ORGANISM: Homo sapiens

<400> SEQUENCE: 9

Ser Ala Ala Gln Leu Pro Gln Lys Ser Ile
 1               5                   10


<210> SEQ ID NO 10
<211> LENGTH: 11
<212> TYPE: PRT
<213> ORGANISM: Mus musculus

<400> SEQUENCE: 10

Leu Leu Gln Lys Ser Ile Leu Glu Arg Lys Glu
 1               5                   10


<210> SEQ ID NO 11
<211> LENGTH: 11
<212> TYPE: PRT
<213> ORGANISM: Homo sapiens

<400> SEQUENCE: 11

Leu Pro Gln Lys Ser Ile Leu Glu Arg Lys Glu
 1               5                   10


<210> SEQ ID NO 12
<211> LENGTH: 10
<212> TYPE: PRT
<213> ORGANISM: Mus musculus

<400> SEQUENCE: 12

Ile Leu Glu Arg Lys Glu Val Leu Val Ala
 1               5                   10


<210> SEQ ID NO 13
<211> LENGTH: 12
<212> TYPE: PRT
<213> ORGANISM: Artificial Sequence
<220> FEATURE:
<223> OTHER INFORMATION: a synthetic peptide
<220> FEATURE:
<221> NAME/KEY: VARIANT
<222> LOCATION: 7
<223> OTHER INFORMATION: Xaa = N-3-(2,
      4-Dinitrophenyl)-L-2,3-diaminopropionyl

<400> SEQUENCE: 13

Pro Leu Ala Gln Ala Val Xaa Arg Ser Ser Ser Arg
 1               5                   10
```